(12) United States Patent
Dickopf

(10) Patent No.: US 9,983,140 B2
(45) Date of Patent: *May 29, 2018

(54) METHOD AND DEVICE FOR DETECTING AN ANALYTE IN A BODY FLUID

(71) Applicant: Roche Diabetes Care, Inc., Indianapolis, IN (US)

(72) Inventor: Kai Dickopf, Wiesloch (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/017,773

(22) Filed: Feb. 8, 2016

(65) Prior Publication Data

US 2016/0153912 A1    Jun. 2, 2016

Related U.S. Application Data

(63) Continuation of application No. 14/578,617, filed on Dec. 22, 2014, now Pat. No. 9,255,885, which is a
(Continued)

(30) Foreign Application Priority Data

Jun. 22, 2012   (EP) .................................... 12173121

(51) Int. Cl.
*G06K 9/00* (2006.01)
*C12Q 1/54* (2006.01)
(Continued)

(52) U.S. Cl.
CPC ............... *G01N 21/78* (2013.01); *C12Q 1/54* (2013.01); *G01N 21/8483* (2013.01);
(Continued)

(58) Field of Classification Search
CPC ............. G06K 9/00; G01N 21/00; C12C 1/00
(Continued)

(56) References Cited

U.S. PATENT DOCUMENTS 4,935,346 A    6/1990  Phillips et al.
6,471,355 B1 * 10/2002  Monson .................. G03B 21/13
                                                            348/383
(Continued)

FOREIGN PATENT DOCUMENTS

CN    1176389 A    3/1998
EP    0021234 B1   1/1981
(Continued)

OTHER PUBLICATIONS

Hoenes, J. et al, "The Technology Behind Glucose Meters: Test Strips", Diabetes Technology and Therapeutics, vol. 10, Supplemental 1, 2008, S-10 to S-26.

*Primary Examiner* — Abolfazl Tabatabai
(74) *Attorney, Agent, or Firm* — Roche Diabetes Care, Inc.

(57) ABSTRACT

A method for detecting at least one analyte in at least one sample of a body fluid is disclosed. Therein, at least one test element (124) is used, the at least one test element (124) having at least one test field (162) with at least one test chemistry (154) is used, wherein the test chemistry (154) is adapted to perform at least one optically detectable detection reaction in the presence of the analyte. The method comprises acquiring an image sequence of images of the test field (162) by using at least one image detector (178). Each image comprises a plurality of pixels. The method further comprises detecting at least one characteristic feature of the test field (162) in the images of the image sequence. The method further comprises correcting a relative position change between the image detector (178) and the test field
(Continued)

(162) in the image sequence by using the characteristic feature, thereby obtaining a sequence of corrected images.

20 Claims, 15 Drawing Sheets

Related U.S. Application Data continuation of application No. PCT/EP2013/062499, filed on Jun. 17, 2013.

(51) Int. Cl.
| | |
|---|---|
| *G01N 21/78* | (2006.01) |
| *G01N 21/84* | (2006.01) |
| *G06K 9/32* | (2006.01) |
| *G06T 7/32* | (2017.01) |
| *G01N 21/77* | (2006.01) |

(52) U.S. Cl.
CPC ....... *G06K 9/00134* (2013.01); *G06K 9/3208* (2013.01); *G06T 7/32* (2017.01); *G01N 2021/7769* (2013.01); *G06K 2009/3225* (2013.01); *G06T 2207/30024* (2013.01); *Y10T 436/144444* (2015.01)

(58) Field of Classification Search
USPC ............... 382/128–137; 435/11, 14, 25, 26; 436/71, 95, 129
See application file for complete search history.

(56) References Cited

U.S. PATENT DOCUMENTS

| | | | | |
|---|---|---|---|---|
| 6,656,697 | B1* | 12/2003 | Ouyang | C12Q 1/26 422/534 |
| 7,867,728 | B2* | 1/2011 | Marfurt | C12Q 1/54 422/423 |
| 9,255,855 | B2* | 2/2016 | Sato | A61B 6/12 |
| 9,255,885 | B2* | 2/2016 | Dickopf | C12Q 1/54 |
| 2008/0095402 | A1 | 4/2008 | Kochi et al. | |
| 2011/0201909 | A1 | 8/2011 | Emery et al. | 600/322 |

FOREIGN PATENT DOCUMENTS

| | | | | |
|---|---|---|---|---|
| EP | 0974303 | A1 | 1/2000 | |
| EP | 1167540 | B1 | 2/2002 | |
| EP | 1359409 | A2 | 4/2003 | |
| EP | 1843148 | A1 | 10/2007 | |
| EP | 2270421 | A1 | 1/2011 | ............ G01B 11/02 |
| WO | 2009103540 | A1 | 8/2009 | |
| WO | 2010094426 | A1 | 8/2010 | |
| WO | 2010094632 | A1 | 8/2010 | |
| WO | 2012010454 | A1 | 1/2012 | |

* cited by examiner

METHOD AND DEVICE FOR DETECTING AN ANALYTE IN A BODY FLUID

CROSS-REFERENCES TO RELATED APPLICATION(S)

This application is a continuation of pending U.S. patent application Ser. No. 14/578,617, filed Dec. 22, 2014, which claims priority to international application number PCT/EP2013/062499, filed Jun. 17, 2013, which claims priority to European patent application number 12173121.0, filed Jun. 22, 2012, each of which is incorporated by reference herein in their entirety.

FIELD OF THE INVENTION

The present application refers to a method, a device and a test system for detecting at least one analyte in a sample of a body fluid. The invention further relates to a computer program with program means for executing the method according to the invention, as well as to a computer system and to a storage medium. Methods, devices, test systems, computer programs and computer systems according to the present invention may be used in medical diagnostics, in order to qualitatively or quantitatively detect one or more analytes in one or more body fluids. Other fields of application of the present invention are possible.

RELATED ART

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods known to the skilled person make use of test elements comprising one or more test chemistries, which, in presence of the analyte to be detected, are capable of performing one or more detectable detection reactions, such as optically detectable detection reactions. With regard to these test chemistries, reference may be made e.g. to J. Hoenes et al.: The Technology Behind Glucose Meters: Test Strips, Diabetes Technology & Therapeutics, Volume 10, Supplement 1, 2008, S-10 to S-26. Other types of test chemistry are possible and may be used for performing the present invention.

Typically, one or more optically detectable changes in the test chemistry are monitored, in order to derive the concentration of the at least one analyte to be detected from these changes. Examples of test fields, test chemistries and methods for monitoring one or more optically detectable changes in the test fields are disclosed in EP 0 821 234 A2. Thus, as an example, the relative remission of the test field may be optically detected as a function of time, up to a defined end point of the chemical detection reaction. From the change in relative remission, the concentration of the analyte may be derived. Similar measurements detecting the quantity of light reflected from the test field as a function of time, up to a defined end point of the detection reaction, are disclosed in EP 0 974 303 A1.

For detecting the at least one change of optical properties of the test field, various types of detectors are known in the art. Thus, various types of light sources for illuminating the test fields as well as various types of detectors are known. Besides single detectors such as photodiodes, various types of devices using detector arrays having a plurality of photosensitive devices are known. Thus, in US 2011/0201909 A1, an arrangement for measuring the concentration of an analyte contained in a sample of a body fluid is disclosed. The arrangement, inter alia, comprises a light source and a detector array. Similarly, EP 1 359 409 A2 discloses an apparatus for determining the concentration of an analyte in a physiological sample. The apparatus includes at least one light source and a detector array.

Further, when using detector arrays, methods are known in the art for detecting errors and artifacts in the images acquired by the detector arrays. Thus, U S 2011/0201909 discloses a correction algorithm which, inter alia, is capable of correcting for imperfections present in the reaction spot observed by the detector array. Similarly, EP 1 359 409 A2 discloses means for determining whether a sufficient amount of sample is present on each of a plurality of different detector areas, wherein only light detected from those areas determined to have sufficient sample is used for determining the concentration of the analyte.

In order to further increase the evaluation of images acquired by detector arrays imaging a test field, statistical methods have been used in the art. Thus, EP 1 843 148 A1 discloses a system for determining the concentration of an analyte in a liquid sample. Therein, frequencies of occurrence of gray values stored in the pixels of the detector array are listed in a histogram, allowing for separating areas wetted by the sample and areas which are not wetted. By evaluating these frequency distributions, the concentration of the analyte may be derived.

EP 2 270 421 A1 discloses a liquid sample analyzing method for analyzing an analyte in a liquid sample by using a test piece on which overflow blocking lines are formed to prevent the liquid sample from flowing to the outside from a passage region of an extended layer. In a state in which the liquid sample is not extended in the passage region, the test piece is measured so as to cross the passage region of the extended layer and the overflow blocking lines. Thus in a state in which a difference in brightness is large between the passage region of the extended region and the overflow blocking lines, it is possible to properly recognize the boundary portions between the passage region of the extended region and the overflow blocking lines.

U.S. Pat. No. 6,471,355 B1 discloses an image alignment system for rear projection in which a portion of the normally changing pixel pattern contains a pixel reference mark, which appears in each of the side-by-side pixel images projected onto a screen. A camera having a field of view large enough to encompass the pixel reference mark of each of the images on the screen captures the location of the pixel reference marks to enable a computer to determine the coordinates of the each of the pixel reference marks and generate a deviation signal represented of the visual misalignment of the side-by-side images. A drive member controllable by the deviation signals from the computer repositions one of the side-by-side images with respect to the other to thereby align the images to produce a single visually seamless image. The camera and computer can continually monitor both of the pixel reference marks to continually generate a deviation signal so that the side-by-side images can automatically be brought into a single visually seamless image.

Further, systems and methods are known which automatically detect a region of interest for evaluation after transfer of a sample onto the test fields. Thus, in WO 2012/010454 A1, a device for detecting at least one analyte in a body fluid is disclosed, the device comprising at least one test element having at least one two-dimensional analysis area. The device further comprises at least one spatial optical detector having a plurality of pixels. The detector is set up for reproducing at least one part of the test element on an image area. The detector is adapted to the test element such that a prescribable minimum number of pixels is provided for each dimension within the analysis image area. Further, a method for automatically detecting a region of interest to be evaluated for determining the analyte concentration is disclosed.

Despite the progress achieved by the above-mentioned known methods and devices, some major challenges remain regarding the precision of the analyte detection. Thus, there is a constant effort for further reducing the sample volume to be applied to the test fields. In order to reduce the discomfort connected to sample generation such as by pricking the patient's finger or earlobe, sample volumes of modern devices typically have been reduced down to volumes below 2 µl, in some cases even below 1 µl or even less. Integrated test systems including so-called micro-samplers have been developed, such as disclosed in WO 2010/094426 A1, comprising a plurality of lancets, each having a lancet tip and at least one capillary for receiving the body fluid during the puncturing process or when retracting the micro-sampler from the patient's skin. The small sample volumes are transferred to test fields inside a cavity into which the micro-sampler is retracted. The small sample volumes and the constant need for reducing the size of the test fields, however, increase the requirements regarding the spatial resolution of the detector arrays and regarding the capabilities of eliminating artifacts and impurities from the images to be evaluated.

A further technical challenge resides in a precise normalization of the measurement data acquired by the optical detectors or detector arrays. In many cases, such as in the above-mentioned devices and methods disclosed by EP 0 821 234 A2, a relative remission of the test fields is detected, requiring the determination of at least one so-called blank or dry value, i.e. a value of reflectance of the test chemistry before onset of the detection reaction. Specifically in case the precise location of sample application onto the test field is unknown, the determination of a blank value, however, is rather challenging, since the blank value itself may be dependent on the precise location on the test field. Thus, in most cases, either blank values in different locations than the location of the sample application on the test field will have to be used, leading to a high uncertainty of the blank value, or, a large number of images of the test field before and after sample application will have to be stored and evaluated, leading to high need for data storage and calculation resources. The latter, however, is specifically disadvantageous for hand-held test devices which typically provide rather limited hardware capabilities.

Further, specifically with regard to the determination of the blank value, mechanical tolerances and tolerances of optical image acquisition have to be considered, specifically in systems having sophisticated transfer mechanisms for transferring the sample onto the test fields. Thus, in systems using micro-samplers, such as in WO 2010/094426 A1, a sample transfer from the micro-samplers onto the test fields takes place by pressing the capillaries of the micro-samplers onto the test fields. This method of sample transfer or other types of sample transfer may lead to a highly structured sample application, requiring a high optical resolution of image acquisition and image evaluation. This type of sample transfer, however, typically implies dynamic processes involving moving parts, which may lead to a displacement of the test fields or parts thereof. Thus, pressing the micro-samplers onto the test fields may lead to a distortion and/or displacement of the test fields. Further, the test fields often are accommodated in a housing of the test elements in a rather loose fashion, such as by simply inserting annular test chemistries into the housing without actually mounting the test fields in a shock-proof fashion. Thus, during use and handling of the test devices, specifically during measurements, the test fields may move, thereby creating inaccuracies regarding acquisition of the blank values and regarding the determination of the actual area of the test fields to be evaluated for analyte determination.

Methods and devices for detecting at least one analyte in at least one sample of a body fluid are disclosed herein, wherein the methods and devices are capable of evaluating even very small sample volumes at a high precision, by widely avoiding artifacts and inaccuracies generated by mechanical disturbances and by sample application in a structured fashion.

SUMMARY OF THE INVENTION

Method and devices for detecting at least one analyte in at least one sample of a body fluid having the features of the claims are disclosed. A computer program, a computer system, a storage medium and a test system having the features of the further claims are further disclosed.

As used herein, the expressions have, comprise and contain as well as grammatical variations thereof are used in a non-exclusive way. Thus, the expression "A has B" as well as the expression "A comprises B" or "A contains B" may both refer to the fact that, besides B, A contains one or more further components and/or constituents, and to the case in which, besides B, no other components, constituents or elements are present in A.

In a first aspect of the present invention, a method for detecting at least one analyte in at least one sample of a body fluid is disclosed. As outlined above, the at least one analyte preferably may comprise one or more substances which typically are contained in a human body or a body of an animal, such as one or more metabolites. Preferably, the at least one analyte may be selected from the group consisting of glucose, cholesterol, triglycerides and lactate. Other types of analytes and/or arbitrary combinations of analytes are possible. Preferably, the method is adapted to detect the analyte with a high specificity. The at least one body fluid generally may comprise an arbitrary type of body fluid, such as blood, interstitial fluid, saliva, urine or any type of other body fluid or combinations of the named body fluids. In the following, without restricting other embodiments, the invention specifically will be explained in the context of a method for detecting glucose in blood and/or interstitial fluid.

The method uses at least one test element, the test element comprising at least one test field. The at least one test field has at least one test chemistry. The test chemistry is adapted to perform at least one optically detectable detection reaction in the presence of the analyte, preferably a color changing reaction. In the context of the present invention, the term test field refers to a continuous or discontinuous amount of test chemistry, which, preferably, is held by at least one carrier, such as by at least one carrier film. Thus, the test chemistry may form or may be comprised in one or more films or layers of the test field, and/or the test field may comprise a layer setup having one or more layers, wherein at least one of the layers comprises the test chemistry. Thus, the test field may comprise a layer setup disposed on a carrier, wherein the sample of the body fluid may be applied to the layer setup from at least one application side, such as from an edge of the test field and/or from an application surface of the test field. The test field may be part of a test element comprising at least one test field and at least one carrier to which the test field is applied.

As used herein, the term test chemistry generally refers to a substance or mixture of substances which is adapted to perform at least one optically detectable detection reaction in the presence of the analyte. Thus, the detection reaction preferably may imply a color change of the test chemistry or of at least one part thereof. With regard to the test chemistry, various possibilities of designing the test chemistry are known in the art. In this regard, reference may be made to the above-mentioned prior art documents. Specifically, reference may be made to J. Hoenes et al.: The Technology Behind Glucose Meters: Test Strips, Diabetes Technology & Therapeutics, Volume 10, Supplement 1, 2008, S-10 to S-26. However, other types of test chemistry are possible. Preferably, the test chemistry comprises at least one enzyme, which preferably directly or indirectly reacts with the analyte, preferably with a high specificity, wherein, further, one or more optical indicator substances are present in the test chemistry, which perform at least one optically detectable property change when the at least one enzyme reacts with the analyte. Thus, the at least one indicator may comprise one or more dyes performing a color changing reaction indicative of the enzymatic reaction of the at least one enzyme and the analyte. Thus, the at least one enzyme may comprise glucose oxidase and/or glucose dehydrogenase. However, other types of enzymes and/or other types of test chemistry or active components of the test chemistry may be used.

The method further comprises acquiring an image sequence of images of the test field. This acquiring of images may comprise acquiring images of the full test field and/or of a specific part of the test field. Thus, at least one viewing window may be defined, such as by a mask and/or a housing of a test element, which provides boundaries of a visible part of the test field, which, in the following, will simply be referred to as a viewing window of the test field. This type of viewing windows e.g. is known from above-mentioned WO 2010/094426 A1.

As used herein, the term image sequence refers to a plurality of images acquired at subsequent points in time. Preferably, the acquisition of the images takes place at equidistant points in time, such as by using a constant frame rate. Thus, frame rates of 20 frames per second, 25 frames per second, 37 frames per second or other types of frame rates may be used. Further, as used herein, the term image refers to a one-dimensional or two-dimensional matrix of information values, wherein each position of the matrix indicates a specific pixel of the image detector and wherein the information value stored in this position of the matrix indicates an optical information acquired by the pixel of the image detector, such as a gray value. As outlined in further detail below, an image may comprise the information values of all pixels of the image detector. Alternatively, only a partial image may be used, such only a specific section of the images. In the following, the term image may refer to both options, i.e. to the option of using the full image or the option of using partial images, only, such as only a pre-defined section of the images.

Consequently, the term image detector (in the following also simply referred to as the detector) refers to an arbitrary detection device having a plurality of optically sensitive sensor elements arranged in a one-dimensional matrix (line detector) or a two-dimensional matrix (array detector). The image sensors of the detector, in the following, will also be referred to as the pixels of the detector. The pixels preferably are arranged in a common plane, which may also be referred to as the detector plane. The matrix of pixels may comprise a straight line of pixels and/or a rectangular array of pixels. However, other types of arrangement of pixels are possible, such as circular arrangements and/or hexagonal arrangements. The pixels themselves are optically sensitive sensor elements, such as optically sensitive semiconductor elements, such as CCD or CMOS sensor elements, preferably CMOS sensor elements.

The method according to the present invention further comprises detecting at least one characteristic feature of the test field in the images of the image sequence. The detection may be performed at least once, which comprises the option repeatedly detecting or attempting to detect the characteristic feature. Thus, the detection of the at least one characteristic feature may also comprise an iterative algorithm, such as an algorithm having 2 or more iterations, such as four iterations, preferably iterations having refined parameters.

As used herein, the term characteristic features refers to an arbitrary feature or irregularity in the test field which is detectable in the images of the image sequence, preferably in all of these images. Thus, the characteristic feature may comprise a characteristic spatial distribution of gray values in the images, indicating random structures and/or regular structures. The characteristic feature preferably denotes a property of the test field itself, such as a property of the test chemistry and/or of another component of the test field. Thus, the characteristic feature may be formed by a visible random structure of the test field, such as by a granularity and/or roughness of the test field. These types of random structures typically are unavoidable when manufacturing the test fields and, within the present invention, may be used without intentionally introducing these characteristic features into the test fields. Alternatively or additionally, the characteristic feature may intentionally be introduced into the test field, such as by introducing one or more positioning marks and/or fiducial marks.

The term detection, as used herein, may refer to an arbitrary algorithm known in the art for detecting one or more patterns, such as known in the field of pattern recognition in the images. The detection specifically may comprise identifying the characteristic feature and/or coordinates of the characteristic feature in the images of the image sequence. Thus, the result of the detection of the characteristic feature specifically may comprise one or more coordinates, such as coordinates of one or more matrices, indicating the position of the characteristic feature in the images of the image sequence. In case the detection should fail and in case the characteristic feature should not be detected in the images of the image sequence, the process of the detection may return an error or default value. However, other embodiments of a detection algorithm may be used, as the skilled person in the field of pattern recognition immediately will recognize.

The detection of the at least one characteristic feature may form an explicit or implicit step of the present method. Thus, the characteristic feature may explicitly be indicated in an output of an intermediate step of the method according to the present invention. Alternatively or additionally, the detecting of the characteristic feature simply may comprise selecting at least one specific part of one or more images of the image sequence, denoting the information contained in this part as the characteristic feature, wherein other images of the image sequence are scanned or searched for this information or similar types of information.

The method further comprises correcting a relative position change between the image detector and the test field in the image sequence by using the characteristic feature, thereby obtaining a sequence of corrected images. As used herein, the term relative position change between the image detector and the test field in the image sequence refers to an arbitrary change of at least one of an absolute position, an angular orientation and a geometric shape of the test field as imaged by the image detector. This relative position change may be due to a change of the position of the image detector and/or a change of the position of the test field.

Further, as used herein, the term correcting refers to an arbitrary algorithm adapted to compensate for the relative position change in the image sequence. Thus, the algorithm may be adapted to transform the information matrix of each image of the image sequence, such as by translating the matrix into at least one direction in space and/or by rotating the information matrix about at least one axis about at least one angle and/or by stretching or compressing the matrix by a specified amount. The correction may individually be adapted for each image of the image sequence, according to the characteristic feature detected in the specific image. Specifically, one of the images of the image sequence may be defined as a reference image, wherein the other images of the image sequence are corrected such that the characteristic feature of all corrected images of the sequence of corrected images may be found at the same position of the matrix.

The sequence of corrected images, in the following, is also referred to as the corrected sequence. By obtaining the corrected sequence according to the present invention, the corrected sequence may be used for detecting the at least one analyte, such as for observing the—optionally time-dependent—change of at least one optically detectable property of the test field due to the detection reaction of the test chemistry with the analyte to be detected. By correcting the image sequence, a high degree of robustness and reliability may be achieved, as opposed to conventional techniques, and most of the above-mentioned shortcomings of known methods and devices are overcome.

The basic method as disclosed above may be developed further in various advantageous ways. Thus, as outlined above, each image of the sequence of images may contain a one-dimensional or two-dimensional or generally n-dimensional matrix of information values, preferably a gray value information, preferably a 4-bit, 8-bit, 12-bit or 16-bit information value.

As outlined above, the correction of the relative position change between the image detector and the test field may comprise an arbitrary correction algorithm. Most preferably, the correction comprises at least one correction selected from the group consisting of: a correction of a translation of an image of the test field on the image detector in at least one spatial direction; a correction of a rotation of an image of the test field on the image detector about at least one rotational axis; a correction of a distortion of an image of the test field on the image detector, preferably a distortion due to a warpage of the test field, such as a correction by using at least one stretching and/or at least one compression. The above-mentioned corrections may easily be implemented by a mathematical correction algorithm transforming the matrix of information values. Appropriate transformations of matrices are known to the skilled person.

As further outlined above, the images of the image sequence preferably are acquired in a constant time sequence, with equidistant time intervals in between acquisition of subsequent images of the sequence. Thus, time intervals of 1/100 s to 5 s may be used, preferably time intervals of 1/64 s to 2 s.

The image detector preferably may comprise at least one detector selected from the group consisting of a line detector having a line of photosensitive sensor elements and a two-dimensional detector having a two-dimensional array of photosensitive sensor elements. The photosensitive sensor elements also are referred to as pixels, as outlined above. Preferably, a two-dimensional array detector may be used, preferably a rectangular array detector. The array preferably comprises at least 3, more preferably at least 5 or even at least 10 pixels in each dimension, such as at least 50 pixels in each dimension. As an example, a two-dimensional array detector may be used comprising 20 to 1000 pixels in each dimension.

Further preferred embodiments refer to the correction of the relative position change. As indicated above, the correction preferably may comprise using at least one image of the image sequence as a reference image. The reference image is kept unchanged during the correction. At least one, preferably more than one and most preferably all other remaining images of the image sequence then may be corrected by using at least one calculational correction of the position of the pixels, such as by using a mathematical transformation of the matrices of these images, such as one or more transformations as listed above. The calculational correction may be chosen such that a correlation between the reference image and the corrected remaining images of the image sequence is maximized. In other words, the calculational correction may be chosen such that, as indicated above, the characteristic feature of the test field may be found in the same place and having the same orientation in each and every image of the corrected sequence of images, at least to a certain and predefined degree of tolerance. As used herein, the term correlation refers to an arbitrary measure for indicating identity or similarity of images and/or features contained in these images. Thus, as an example, one or more correlation coefficients may be used for quantifying the similarity and/or identity of the images, such as empiric correlation coefficients and/or Pearson-correlations.

As outlined above, the calculational correction may comprise a shifting of the pixels of the remaining images of the image sequence in at least one spatial direction. This shifting of pixels may be performed by a translational transformation of the matrix of information values representing the images. The shifting may be chosen such that the correlation between the reference image and the corrected remaining images is maximized. The shifting may be individually chosen for each image of the remaining images of the image sequence.

Additionally or alternatively to a shifting of the pixels of the remaining images, a rotation may be used. Thus, the calculational correction may comprise at least one rotation of the remaining images of the image sequence about at least one rotational axis by at least one rotation angle. The rotational axis and/or the rotation angle may be chosen such that the correlation between the reference image and the corrected remaining images may be maximized. Again, the rotational axis and/or the rotation angle may individually be chosen for each image of the remaining images of the image sequence. Further, the calculational correction may comprise a plausibility check. Thus, in case a calculational correction should be required which turns out to exceed a predetermined limit value, the correction may return an error and/or may be interrupted. Similarly, in case more than one calculational correction should turn out to be plausible, such as by detecting more than one pattern match, more than one high or plausible correlation, an error may be returned and/or the calculational correction may be aborted.

Further preferred embodiments of the present invention refer to the above-mentioned characteristic feature. One or more characteristic features may be used for performing the correction. The characteristic feature may comprise at least one feature selected from the group consisting of: a roughness of the test field detectable in the images of the image sequence; a granularity of the test chemistry of the test field detectable in the images of the image sequence; faults of the test field detectable in the images of the image sequence; at least one, preferably at least two, fiducial marks comprised in the test field and detectable in the images of the image sequence. As used herein, the term fault may refer to an arbitrary imperfection in the test chemistry and/or the test field, such as dirt, fibers, cracks or any other type of irregularity. Other types of characteristic features may be used.

The method further may comprise at least one step of deriving the actual analyte concentration from the image sequence or corrected image sequence. Preferably, a concentration of the analyte is detected by detecting at least one optical property of the test chemistry and/or by detecting at least one change of at least one optical property of the test chemistry due to the optically detectable detection reaction of the test chemistry and the analyte. Thus, the at least one optical property may comprise at least one optical property selected from the group consisting of a color, an absolute remission and a relative remission. As used herein, the term color refers to a specific absorption of light in at least one predetermined spectral range, which may reside in the visible and/or the ultraviolet and/or the infrared spectral region. The term remission refers to an undirected reflection of light, such as scattered light. Thus, for determining the remission, at least one light source may be used for illuminating the test field from at least one detection side, and light reflected and/or scattered from the test field may be detected by the above-mentioned detector, preferably at an angle different from the angle of illumination of the test field. The term relative remission refers to a normalized remission, wherein, preferably, a specific remission is used as a norm value. Thus, when detecting changes of the at least one optical property after application of the sample of the body fluid to the test field, a so-called blank value of the remission before application of the sample may be used for normalizing the subsequent remission values, in order to obtain the relative remission. The blank value is also referred to as a dry empty value. At least one of these values may be used. In case a normalization (also referred to as a standardization) is performed, such as for creating values of a relative remission, the normalization may take place on the basis of a full image, on the basis of a partial image as well as on a pixel-by-pixel basis. Thus, on a pixel-by-pixel basis, an information value of each pixel of an image may be divided by the information value of a corresponding pixel of a blank image.

The at least one optical property of the test chemistry and/or the at least one change of the at least one optical property may be derived from one information value, more than one information value or all information values contained in the matrices of one, more than one or all of the images of the image sequence or the corrected image sequence. Examples will be given in further detail below.

The at least one sample of the body fluid may be applied to the test field during acquisition of the image sequence.

Consequently, the image sequence may be sub-divided into two or more image sequences, depending on the point of time of acquisition of the respective image. Thus, the image sequence may comprise a blank image sequence, wherein the blank image sequence may comprise a plurality of blank images acquired before applying the sample of the body fluid to the test field. Preferably, the blank image sequence may comprise all images acquired before a sample application. The blank image sequence may also be referred to as the dry empty image sequence.

The blank image sequence preferably may be used for deriving at least one information regarding the test field before sample application. For this purpose, preferably, the corrected blank images are used, i.e. the blank images after performing the above-mentioned at least one correction of the relative position change between the image detector and the test field in the sequence of blank images. Preferably, at least one averaged blank image is derived from the blank images of the blank image sequence after performing the correction of the relative position change of the blank images of the blank image sequence. As used herein, the term averaged image, or, specifically, the term averaged blank image, refers to a result of an arbitrary averaging process of several images, wherein a matrix of average values is generated. Thus, the averaging may be performed on a pixel-by-pixel basis, by averaging corresponding fields of the matrices. Thus, in case of a two-dimensional matrix, an averaging of corresponding pixels of the matrices may be performed, thereby generating an averaged value for each field of the matrices. The averaging generally may comprise any type of known averaging method, such as a weighted averaging, a geometric averaging or an arithmetic averaging. The averaged blank image thus may be a matrix having the same number of fields in each dimension as the corrected images of the corrected blank image sequence, wherein each field of the matrix of the averaged blank image contains an averaged information value as a result of an averaging process over the corresponding fields of the corrected blank images.

The averaged blank image preferably may be derived in a continuous process during acquiring the images of the image sequence. In this continuous process, preferably, a preliminary averaged blank image may be derived from the corrected blank images acquired so far. New acquired blank images may be used for revising the preliminary averaged blank image. Thus, with each newly acquired blank image, the preliminary averaged blank image may be updated, thereby generating a new preliminary averaged blank image. The final version of the preliminary averaged blank image, i.e. the preliminary averaged blank image derived after incorporating the last corrected blank image of the corrected blank image sequence, may then be used as the final averaged blank image. Generally, information of corresponding pixels of the corrected blank images of the blank image sequence may be used for deriving an information of a corresponding pixel of an averaged blank image. Thus, generally, the information of corresponding pixels of the corrected blank images may be combined by at least one linear combination and/or by at least one averaging operation for deriving the corresponding pixel of the averaged blank image. Thus, all pixels $(i, j)_n$ of all corrected images n of the corrected blank image sequence may be combined by at least one linear combination and/or by at least one averaging operation, for deriving the corresponding pixel $(i, j)_{av}$ of the averaged blank image, for all i, j of the matrices.

The analyte may be detected by using the blank image sequence, preferably by using the corrected blank image sequence and more preferably by using the averaged blank image.

Additionally or alternatively, the method may comprise at least one additional step of determining at least one touchdown image, preferably at least one corrected touchdown image. As used herein, the term touchdown image refers to an image of the image sequence acquired precisely at the moment of sample application, which is also referred to as the moment of touchdown, or to the image of the image sequence acquired after the moment of sample application which is acquired at a moment which is closest to the moment of sample application as compared to all other images of the image sequence. Correspondingly, as used herein, the term corrected touchdown image refers to a corrected image of the corrected image sequence acquired precisely at the moment of sample application, which is also referred to as the moment of touchdown, or to the corrected image of the corrected image sequence acquired after the moment of sample application which is acquired at a moment which is closest to the moment of sample application as compared to all other corrected images of the corrected image sequence.

Preferably, the touchdown image is an image visualizing the test field or at least one part thereof after sample application, before any detection reaction has taken place, at least within the tolerance is provided by a detection limit of the image detector. Thus, the touchdown image is an image of the test field or at least one part thereof with the sample of the body fluid having wetted the test chemistry are at least one part thereof, wherein, however, preferably no detection reaction of the test chemistry has taken place. Thus, the touchdown image may provide information regarding optically detectable changes of the test field or at least one part thereof over images acquired before sample application, such as changes due to a wetting of the test chemistry with the sample of the body fluid and/or changes of the test field due to mechanical deformation of the test field due to the sample application, such as mechanical information due to contacting the test field with a capillary and/or a puncture element such as lancet in order to transfer the sample of the body fluid onto the test field.

Thus, in addition or alternatively to using one or more of the blank image sequence, the corrected blank image sequence and the averaged blank image, the touchdown image or the corrected touchdown image might be used for detecting the analyte.

As an example, the analyte might be detected by using at least one image, preferably at least one corrected image, acquired after sample application and/or any information derived thereof, such as a time sequence of average values over these images or corrected images or parts thereof. Additionally, since the sample application might introduce artifacts in the image sequence or corrected image sequence, the detection of the analyte might take into account at least one information derived from the above-mentioned touchdown image or corrected touchdown image. Thereby, as an example, changes in the image sequence or corrected image sequence due to the sample application might fully or partially be corrected, such as changes induced by wetting of the test field and/or changes induced by mechanical deformation of the test field. Additionally or alternatively, the detection of the analyte might take into account at least one information derived from the blank image sequence, such as at least one information derived from the averaged blank image. Thereby, as an example, influences of batch-to-batch variations of the test field and/or influences of an illumination of the test field might fully or partially be corrected.

Thus, the analyte may be detected by comparing the images of the sequence of the corrected images with one or more of the touchdown image and the blank image sequence, preferably with the averaged blank image and/or the touchdown image. As used herein, the term comparing refers to an arbitrary process suited to derive an information regarding a deviation are differences of information values contained in images. Thus, the term comparing specifically may refer to a formation of a difference value between two information values and/or to a formation of a quotient of two information values.

The comparison preferably may be performed on a pixel-by-pixel basis, by comparing each pixel of the corrected images of the sequence of corrected images with corresponding pixels of the touchdown image or corrected touchdown image and/or with corresponding pixels of images of the blank image sequence, preferably the corrected blank image sequence and more preferably with pixels of the averaged blank image. Thus, a pixel-by-pixel difference and/or a pixel-by-pixel ratio may be derived, generating a matrix of ratios by dividing corresponding pixels of the corrected images and the corresponding pixels of the touchdown image and/or the blank images, preferably the averaged blank image, and/or by subtracting corresponding pixels of the images of the sequence of corrected images and the corresponding pixels of the touchdown image or corrected touchdown image and/or the corresponding pixels of the blank images, preferably the averaged blank image.

As outlined above, the comparison between the images of the sequence of corrected images with the touchdown image and/or the blank image sequence, preferably with the averaged blank image, may be performed on a pixel-by-pixel basis, thereby deriving a matrix of comparison values, such as a matrix containing differences and/or quotients.

As an example, a comparison matrix may be derived and used for analyte detection, preferably for determining the concentration of the analyte. The information value of each pixel of the comparison matrix preferably may be a difference of corresponding information values of the pixels of the image or corrected image and the pixels of the touchdown image or corrected touchdown image, the difference being divided by the information value of the corresponding pixel of at least one blank image or corrected blank image, preferably the averaged blank image. Examples of this type of comparison matrix will be given in further detail below. As an example, in case the information value pixel (i, j) of the $n^{th}$ image or corrected image of the image sequence are denoted by $I_n(i, j)$, the information value of the averaged blank image is denoted by $B(i, j)$ and the information value of pixel (i, j) of the touchdown image is denoted by $T(i, j)$, the corresponding pixel of the comparison matrix $C_n$ may be derived according to the following formula:

$$C_n(i, j) = \frac{I_n(i, j) - T(i, j)}{B(i, j)}$$

In order to detect the analyte, specifically for deriving a concentration of the analyte in the at least one sample of the at least one body fluid, the at least one comparison matrix may be evaluated further. Thus, an average value of the information contained in this comparison matrix may be evaluated or, alternatively, only part of this comparison matrix may be evaluated, such as information values within a region of interest of the comparison matrix, as will be explained in further detail below.

Most preferably, the information contained in each pixel of the images of the sequence of corrected images after application of the sample of the body fluid to the test field may be divided by the information contained in the corresponding pixel of at least one blank image, preferably the averaged blank image, thereby creating a normalized information for each pixel. Consequently, a sequence of corrected relative images may be created, each corrected relative image having pixels containing the normalized information of the respective pixel. Therein, at least one averaged normalized value may be created over at least part of the sequence of corrected relative images, preferably over a region of interest of the corrected relative images. Preferably, the normalized value may be an average value over the part of the sequence of the corrected relative images, preferably over the region of interest of the corrected relative images. The averaged normalized value preferably may be used for deriving a concentration of the analyte in the body fluid. The averaged normalized value preferably may be monitored as a function of time after application of the sample of the body fluid to the test field. Examples of this method will be given in further detail below. However, it should be noted that other types of deriving the concentration of the at least one analyte in the sample of the body fluid may be realized.

Further embodiments of the present invention relate to the detection of boundaries of the test field. Preferably, boundaries of the test field and/or boundaries of a visible window of the test field may be detected in the sequence of corrected images. The detection may take place in each corrected image of the sequence of corrected images, in a group of corrected images or in one corrected image. As an example, the detection of the boundaries of the test field and/or boundaries of a visible window of the test field may take place in the corrected blank image sequence and/or in the averaged blank image. As used herein, the term boundaries refers to one, two, three or four borderlines of the test field, which determine a lateral extension of the test field and beyond which an evaluation of the image shall not be performed. Thus, as indicated above, the test field may be delimited by one or more borderlines beyond which no test chemistry is applied to a carrier of a test element. Additionally or alternatively, as outlined above, the optically detectable reaction may be observed by the detector via a viewing window defined by one or more windows in a mask or housing of a test element, which fully or partially covers the test field. In this regard, reference may be made to the above-mentioned WO 2010/094426 A1, disclosing a housing having windows through which a reaction of the test chemistry may be observed. Thus, the method according to the present invention may comprise a detection of one or more boundaries of the test field and/or boundaries of the visible window of the test field in one, more than one or even all of the images of the sequence of corrected images and/or in the corrected blank image sequence and/or in the averaged blank image.

For detecting the boundaries of the test field and/or the boundaries of the visible window of the test field, various methods may be used, which, generally, are known to the skilled person. Thus, one or more threshold methods may be used, comparing the information of the pixels of the corrected images with one or more thresholds. Generally, since, after the above-mentioned correction process, all images of the sequence of corrected images should be oriented and/or positioned correctly, it may be sufficient to determine the boundaries of the test field and/or the boundaries of a visible window of the test field in one of the corrected images of the sequence of corrected images, since the position of these boundaries may be transferred to the other corrected images of the sequence. Thus, as an example, the boundaries of the test field and/or the boundaries of the visible window of the test field may be defined as a function of position coordinates in the sequence of corrected images, wherein the function preferably is applicable to all corrected images of the sequence of corrected images. Thus, the sequence of corrected images even may be oriented and/or corrected in such a way that the boundaries of the test field and/or the boundaries of the viewing window are oriented parallel to the axes of a coordinate system of the matrices of the sequence of the sequence of corrected images.

Further preferred embodiments refer to a detection of the application of the sample of the body fluid onto the test field. Thus, in a preferred embodiment of the method according to the present invention, the moment of application of the sample of the body fluid onto the test field is detected in the image sequence, preferably in the corrected sequence of images. As used herein, the term moment of application refers to a point in time at which the sample transfer of the sample of the body fluid onto the test field takes place. As used herein, the term time may refer to an arbitrary parameter or variable indicating a progress of the method. This parameter may be a time parameter, an internal clock of a device performing the method or may even be a number or indicator of a specific image of the sequence of images in which the sample transfer is detected. Since, preferably, the images are acquired at predetermined points in time, the identifier of the specific image indicating the sample transfer denotes a specific moment in the process, thereby denoting the moment of application of the sample of the body fluid onto the test field.

In the following, the moment of application of the sample of the body fluid onto the test field is also referred to as the moment of sample application, the moment of touchdown, the moment of application or the moment of transfer. This moment may actually denote a specific point in time or even a period of time, since the sample transfer typically takes place over a period of time. In case the moment of transfer actually is a period of transfer, the beginning of the period of transfer may be denoted as the specific moment of transfer. Alternatively or additionally, the acquisition time of the first image of the sequence of images, in which a sample transfer is detected, may be denoted as the moment of transfer.

Various methods may be used for detecting the moment of application. Thus, the moment of application may be detected by observing one or more changes of the information contained in the image sequence, preferably the corrected image sequence. Thus, changes of averaged information contained in the images of the image sequence may be observed. Therein, the uncorrected image sequence and/or the corrected image sequence may be used. Preferably, the moment of application of the sample of the body fluid onto the test field may be detected by observing one or more changes in the corrected images of the corrected image sequence.

For detecting the moment of application, neighboring images of the image sequence, preferably the corrected image sequence, may be compared after correction. The comparison preferably may be performed by using neighboring averaged images. Thus, for each image or corrected image, an average value may be derived, such as by averaging all information values contained in the images or corrected images and/or by averaging over a predetermined group or determinable group of information values contained in these images. Thereby, a difference averaged value for each pair of neighboring images may be derived, indicating the difference between neighboring images on neighboring corrected images. The moment of application of the sample onto the test field may be detected by comparing the difference averaged value with at least one threshold. Other types of detection of the moment of application may be possible.

As outlined above, additionally to detecting the moment of sample application, a touchdown image may be identified in the image sequence, or, correspondingly, a corrected touchdown image may be identified in the corrected image sequence. As used herein, the touchdown image is the image of the image sequence after sample application acquired closest to the moment of sample application. Thus, the touchdown image may be acquired precisely at the moment of sample application or closely after the moment of sample application. Thus, as soon as the moment of sample application is identified, such as by using one or more of the methods disclosed above, the touchdown image is the image acquired at the moment of sample application or, in case no image should have been acquired at this moment, the next image of the image sequence, acquired at an acquisition time closest to the moment of sample application.

The touchdown image or corrected touchdown image preferably may be used for detecting a region of interest, as will be outlined in further detail below.

Further embodiments of the present invention refer to the fact that, after application of the sample onto the test field, typically, only part of the test field actually performs a detectable reaction in dependence of the concentration of the analyte and, thus, only part of the test field is suited for evaluation for determining the analyte concentration. Thus, in a preferred embodiment of the present invention, after application of the sample of the body fluid onto the test field, at least one region of interest is determined in the image sequence. This region of interest may be determined in one image of the image sequence, a plurality of images in the image sequence or in all images of the image sequence. Preferably, the region of interest is determined in one corrected image, a plurality of corrected images or in all corrected images of the corrected sequence of images. Thus, by performing the above-mentioned correction of the image sequence, the region of interest simply may be defined by defining coordinates in the corrected image sequence, since the orientation and/or positioning of the corrected images within the corrected image sequence remains constant.

As used herein, the term region of interest refers to a group or set of pixels, defined by a group or set of pixel coordinates, in the matrices of the images of the image sequence, preferably in the corrected images of the corrected image sequence, wherein the set or group of pixels are considered to contain information values to be considered for subsequent analysis, for the purpose of qualitatively or quantitatively detecting the at least one analyte in the sample of the body fluid. In an extreme case, the region of interest may comprise as little as one single pixel. However, typically, the region of interest comprises a plurality of pixels.

Thus, the region of interest may define a set or group of pixels in the images or corrected images, wherein the information values contained in these pixels are considered for subsequent analysis, whereas other information values of the matrices which are not contained in the set or group of pixels may be neglected, or which may be considered at a lower degree or at a lower weighting. Thus, the region of interest may define a set or group of pixels containing information values contained in one or more of the images which are considered to be significant for determining the analyte concentration, whereas other pixels are considered insignificant or less significant.

Preferably, the region of interest is determined by a digital mask, which assigns the value 1 (to be considered for subsequent analysis) or 0 (not to be considered for subsequent analysis) for all pixels of the matrices of the images or corrected images of the image sequence or corrected image sequence. Thus, preferably, one matrix, a plurality of matrices or all matrices of the image sequence or, preferably, of the corrected image sequence may be modified by the mask in such a way that all information values positioned outside the region of interest are replaced by 0, whereas all information values inside the region of interest are kept unchanged. Further examples will be given below.

In order to determine the region of interest, preferably in the corrected image sequence, various methods may be used. Preferably, at least one corrected image may be acquired before or during application of the sample of the body fluid onto the test field, and at least one corrected image may be acquired after application of the sample of the body fluid onto the test field. As an example of an image or corrected image acquired during sample application, reference may be made to the touchdown image or corrected touchdown image as defined above. Thus, the image acquired during sample application may be the touchdown image as defined above.

The image acquired after sample application, preferably the corrected image acquired after sample application, preferably may be an image acquired at a predetermined point in time after the moment of sample application. Preferably, the point in time may be chosen such that the detection reaction has already led to a significant change in the information values or at least some of the information values contained in the image. As an example, the image acquired after sample application may be acquired at a predetermined time span after the moment of sample application, such as a time span of 0.5 seconds to 4 s, preferably a time span of 0.7 s to 2 s and more preferably a time span of 1 s.

As a preferred example, the image acquired before or during sample application may be the above-mentioned touchdown image. The image acquired after sample application may be an image acquired 1 second after the moment of sample application.

For determining the region of interest, the at least one corrected image acquired before or during sample application may be compared to the at least one corrected image acquired after sample application on a pixel-by-pixel basis, i.e. by comparing each pixel of the corrected image acquired before or during sample application with the corresponding pixel of the corrected image acquired after sample application. Thereby, a difference value may be generated for each pixel, such as by subtracting the information value of the pixel of the corrected image acquired before or during sample application from the information value of the corresponding pixel of the corrected image acquired after sample application. Thereby, a difference value may be generated for each pixel, wherein the difference value denotes a difference of the information contained in corresponding pixels of the corrected images acquired before or during sample application and after sample application onto the test field. Thereby, a difference matrix may be generated, wherein the differences of these images may be provided for each pixel.

Based on these difference values, again, a threshold method may be used for determining the region of interest. Thus, pixels may be classified as pixels belonging to the region of interest or as pixels not belonging to the region of interest based on the difference values. Thus, the difference values for each pixel may be compared to one or more thresholds, wherein differences exceeding (by itself or in their absolute values) the threshold may be classified as pixels belonging to the region of interest, whereas other pixels may be classified as pixels not belonging to the region of interest. Thereby, by determining the positions of the pixels belonging to the region of interest, a set or group of positions may be derived which, by itself, may be defined as the region of interest within the matrices.

As outlined above, at least one corrected image is acquired before or during sample application, and at least one corrected image is acquired after sample application. Preferably, the acquisition time of the corrected image acquired before or during sample application and the acquisition time of the corrected image acquired after sample application are rather close to the moment of application of the sample of the body fluid onto the test field. Thus, preferably, the acquisition time of the corrected image acquired before or during sample application is chosen to be no more than 1 s before the moment of sample application, and the acquisition time of the corrected image acquired after sample application is chosen no more than 1 s after the moment of sample application. By this choice of the acquisition times, it may be ensured that the difference values defined above are mostly due to the wetting of the test field and/or the test chemistry by the sample of the body fluid.

The region of interest is determined such that the region of interest may fully reside within the test field or, more preferably, within the boundaries of the visible window of the test field, as defined above.

As outlined above, when determining a difference matrix comprising the difference values for each pixel derived from the comparison of the corrected images acquired before or during sample application and after sample application, at least one threshold method may be used for classifying the pixels, in order to derive the region of interest. Various types of threshold methods are known in the art and may be used for the purpose of determining the region of interest. Thus, one or more thresholds may be defined by empiric measurements of typical samples, thereby empirically deriving the at least one threshold for classifying the pixels into pixels belonging to the region of interest and pixels not belonging to the region of interest. Thus, at least one threshold may be defined for each dimension, such as one threshold for an x-direction and one threshold for a y-direction. More preferably, the at least one threshold method may comprise an Otsu method. Thus, the pixels containing the difference values may be classified into two sets or groups, one group containing the pixels belonging to the region of interest and one group not belonging to the region of interest. The groups may be chosen by choosing at least one threshold value delimiting the groups, wherein pixels having difference values above the threshold are assigned to a first group, and pixels having difference values below the threshold are assigned to the second group. Therein, the threshold may be chosen such that the variance between the difference values within the same class is minimized, whereas the variance between the difference values belonging to different classes is maximized. However, in addition or alternatively to the Otsu method, other types of threshold methods may be used.

As outlined above, the region of interest may be given as an image mask. This image mask may be generated denoting the pixels belonging to the region of interest. Thus, the image mask may be adapted to replace all information values of the images, preferably the corrected images, positioned outside the region of interest by 0, whereas the information values of the pixels located within the region of interest may be kept unchanged. This image mask may be applied to one image, preferably one corrected image, to a plurality of images, preferably a plurality of corrected images, or to all images, preferably to all corrected images. Preferably, the image mask may be a binary image mask, multiplying all information values of pixels inside the region of interest with 1, whereas the information values of pixels located outside the region of interest are multiplied with 0.

The region of interest may be used for detecting the at least one analyte in the sample of the body fluid in various ways. Thus, preferably, only pixels belonging to the region of interest in the sequence of corrected images may be used for detecting the analyte in the sample of the body fluid.

Further, as outlined above, the analyte concentration may be derived from the image sequence or corrected image sequence, such as by using at least one evaluation algorithm. The evaluation algorithm may be predetermined or may be determinable. Further, a choice of the evaluation algorithm out of a plurality of potential evaluation algorithms may be made, based on the above-mentioned difference matrix containing differences of information values of the images acquired before or during sample application and of images acquired after sample application. Thus, on the basis of these differences, such as on the basis of an averaged difference over the full images or a part of these images, such as over the above-mentioned region of interest, an appropriate evaluation algorithm may be chosen.

Thus, as an example, the above-mentioned difference matrix containing differences of information values of an image acquired 1 second after the moment of sample application and the touchdown image may be used. Based on the difference values contained in this difference matrix, such as based on an averaged difference value over all difference values contained in the difference matrix or over the region of interest within the difference matrix, a decision may be made on an appropriate evaluation algorithm to be used for determining the analyte concentration from the image sequence, preferably the corrected image sequence. Thus, in case the averaged difference value fulfills at least one predetermined condition, an evaluation algorithm assigned to this predetermined condition may be chosen. As an example, the predetermined condition may comprise a comparison with one or more thresholds.

In a further aspect of the present invention, a computer program is disclosed. The computer program comprises program means for executing the method steps of the method according to one or more of the embodiments of the method according to the present invention, such as the embodiments disclosed above or the embodiments disclosed in the following. Thus, program means may be provided for executing the step of acquiring the image sequence of images of the test field by using the image detector, program means for detecting at least one characteristic feature of the test field in the images of the image sequence and program means for correcting the relative position change in the image sequence, thereby generating the sequence of corrected images. Further, program means may be provided for executing the additional optional method steps as outlined above or as outlined in the following. The program means generally each may comprise one or more computer-readable commands adapted to make a computer or computer network execute the method steps when the computer program is executed on the computer or computer network. Preferably, the program means may be stored on a storage medium, such as a volatile or non-volatile computer storage medium, readable by a computer or computer network, such as on at least one computer-readable data carrier. As used herein, the term computer may refer to an arbitrary data processing device. Thus, the term computer may refer to a stationary data processing device and/or to a handheld device, such as a portable computer, a handheld computer, a pocket-size portable device or any other type of portable device.

As used herein, the term portable generally may refer to a device which may be carried by a human person, such as in a pocket. Thus, preferably, the portable device generally may have a weight which preferably does not exceed 1 kg and, more preferably, does not exceed 500 g. Further, the portable device preferably has a volume which does not exceed 1000 $cm^3$ and, more preferably, does not exceed 500 $cm^3$.

Further, a computer system, such as a system comprising one or more computers and/or a computer network, is disclosed, the computer system having at least one processor for loading the computer program according to the present invention and for executing the computer program. The computer system itself may fully or partially be part of a device for detecting at least one analyte in at least one sample of a body fluid, as disclosed in further detail below. Other implementations of the computer system may be possible.

In a further aspect, a storage medium is disclosed, wherein a data structure is stored on the storage medium, wherein the data structure is adapted to perform the method according to one or more of the embodiments of the method according to the present invention, after having been loaded into a computer or computer network.

In a further aspect of the present invention, a device for detecting at least one analyte in at least one sample of a body fluid is disclosed. The device comprises at least one test element receptacle for receiving at least one test element having at least one test field with at least one test chemistry. For potential embodiments of the test element, reference may be made to the disclosure of the method in one or more of the embodiments disclosed above or disclosed in further detail below.

The at least one test element generally may comprise one or more test elements, wherein various types of test elements are usable within the present invention. Thus, the device may comprise exactly one test element. Alternatively, the device may comprise a plurality of test elements. Thus, as an example, the device may comprise a magazine, the magazine containing precisely one test element, or, alternatively, the device may comprise a magazine, the magazine containing a plurality of test elements.

Thus, test strips, test tapes, test cassettes or test magazines comprising a plurality of test elements may be used. In this regard, reference may be made to the prior art documents listed above. Other types of test elements may be usable. With regard to the test element receptacle, any type of receptacle adapted for receiving the at least one test element is usable, wherein the receptacle may be adapted to hold and/or position the at least one test element within the device, such as in at least one measurement position and/or in at least one sample application position. Thus, at least one measurement position and/or at least one sample application position of the test element or of a part thereof may be provided. The test element, as indicated above, may comprise the at least one test field. The test element may further optionally comprise at least one puncture element, such as at least one lancing element, which, preferably, may be mounted movably with regard to the test field, in order to perform a puncture motion, a sampling motion or a lancing motion, thereby generating an incision in a skin surface. Preferably, the test field remains in a fixed position during the puncture, sampling or lancing motion, wherein a sample of a body fluid is transferred onto the test field, such as by a capillary action and/or by pressing the puncture element or a part thereof onto the test field after the puncture, sampling or lancing motion.

The device further comprises at least one image detector, also referred to as a detector, for acquiring an image sequence of images of the test field. With regard to potential embodiments of the image detector, reference may be made to the detectors mentioned above. The device may further comprise one or more data storage devices adapted to store the images of the image sequence, such as one or more volatile or non-volatile data storage devices.

With regard to potential embodiments of the image detector, reference may be made to the disclosure of the method above. Specifically, the image detector may comprise at least one line detector and/or at least one two-dimensional image detector, preferably a CCD line sensor, a CMOS line sensor, a two-dimensional CCD array sensor, a two-dimensional CMOS array sensor or an arbitrary combination of the named sensor systems and/or other sensors.

The detector or image detector, besides the plurality of pixels, may further comprise one or more additional elements. Thus, preferably, the detector may comprise one or more light sources adapted to generate light in the ultraviolet and/or visible and/or infrared spectral range. The at least one optional light source may be adapted to illuminate at least part of the at least one test chemistry and/or at least part of the at least one test field. Thus, preferably, the detector comprises at least one light source generating light for illuminating at least part of the test field, wherein the plurality of pixels is adapted to detect light propagating from the test field. Therefore, preferably, the at least one light source and the plurality of pixels are arranged on the same side of the test field. Various possibilities regarding the nature of the light propagating from the test field to the plurality of pixels of the detector are feasible. Without restricting these possibilities, the light generated by the at least one light source may be referred to as the excitation light, and the light propagating from the test field to the plurality of pixels may be referred to as the detection light or response light. Generally, as an example, the detection light may be or may comprise excitation light which is fully or partially reflected or diffracted by the test field. Additionally or alternatively, the detection light may be or may comprise light emitted by the test chemistry or parts thereof, such as fluorescence (e.g. as in EP 1 780 288 B1) and/or phosphorescence light. Thus, generally, the excitation light and the detection light may have the same wavelength or the same spectral properties or may have different wavelengths or different spectral properties. Preferably, the angle of incidence of the excitation light onto the test field differs from the angle of emission of the detection light. Thus, preferably, no excitation light directly reflected from the test field is detected by the plurality of pixels. However, other possibilities are feasible.

In the following, a preferred embodiment of a detector is disclosed. The detector may be used as the detector in the methods and devices according to the present invention. However, the detector may also be realized in an isolated way, without the further details of the present invention or with details referring to the detector only, without other elements of the present invention. The detector comprises at least one light source, as outlined above. The detector further comprises the plurality of optically sensitive sensor elements, as disclosed in further detail above. The detector further comprises at least one wavelength-converting material adapted to convert the wavelength of light passing the wavelength-converting material to a different wavelength, preferably a longer wavelength. Thus, the at least one wavelength-converting material may be comprised in one or more layers. Preferably, the wavelength-converting material may be comprised in at least one coating. The coating may fully or partially cover the plurality of pixels of the detector. The pixels of the detector may be comprised in the image sensor of the detector, wherein the image sensor is fully or partially covered by the at least one coating comprising the at least one wavelength-converting material.

Preferably, the at least one light source is adapted to generate ultraviolet light. However, other types of light sources may be used in addition or alternatively. The at least one wavelength-converting material preferably may be adapted to convert light in the ultraviolet spectral range or light in the blue spectral range into visible light in the green or red or even infrared spectral range. Thus, the at least one wavelength-converting material may be adapted to convert light into a spectral range of maximum sensitivity of the pixels.

Various types of wavelength-converting materials are known in the art and, partially, are commercially available. Thus, the wavelength-converting material may comprise one or more fluorescent materials and/or one or more phosphorescent materials. Organic and/or inorganic wavelength-converting materials may be used, such as one or more fluorescent dyes. Thus, as an example, quantum dot materials, Europium complex materials or fluorescent dyes known from display technology or lighting technology may be used as wavelength-converting materials.

The detector may comprise an image sensor comprising the plurality of pixels, such as a CMOS or CCD image sensor chip. The image sensor may have one or more coatings comprising the wavelength-converting material, such as at least one fluorescent material. As an example, the wavelength-converting material may be adapted to convert photons having a wavelength of 360 nm into photons of 600 nm. Other types of conversion are possible. A large number of dyes are available having a sufficient quantum efficiency and durability. Even though the conversion may imply a certain loss in photon flux, mostly due to geometric reasons and sensitivity, the wavelength conversion in total may increase the detection efficiency due to a better sensitivity of the image sensor chip at the longer wavelength. Thus, standard CMOS image sensor chips typically exhibit a maximum efficiency in the range of 600 to 900 nm. Sensitivity in the ultraviolet or blue spectral range on the other hand may be decreased to 10% or even less than 1%. Thus, by using the wavelength-converting material, a high increase in detection efficiency may be achieved.

Further, the wavelength-converting material specifically may be adapted to the specific circumstances of detection, specifically with regard to the conversion properties. Thus, typically, fluorescence dyes may convert light in the range of 360 nm into light having a wavelength of 600 nm or more.

In addition to the at least one wavelength-converting material, the detector may comprise one or more filter materials adapted to fully or partially filter one or more wavelength of light passing the filter material. Thus, a layer setup may be used, such as a coating on the image sensor chip, comprising one or more layers having the at least one wavelength-converting material and one or more layers having the at least one filter material. Additionally or alternatively, the at least one wavelength-converting material and the at least one filter material may be comprised in one and the same layer. Thus, by using the filter material, unwanted light may be eliminated and/or suppressed. By using this or other techniques, an efficient image sensor, such as an efficient CCD or CMOS image sensor chip, may be realized, for use in the ultraviolet spectral range, such as for use at a wavelength of 360 nm, which may specifically be adapted for the present invention. However, other types of detectors may be used additionally or alternatively.

The wavelength-converting material may further be used in simple one-dimensional photo diodes, such as silicon photo diodes like BPW34 photo diodes, as available e.g. from Vishay Semiconductor GmbH, D-74025 Heilbronn, Germany. One general advantage resides in the relatively low costs, since silicon photo diodes typically are available in a price range approximately 2 orders of magnitude below photo diodes having a maximum sensitivity in the ultraviolet or blue spectral range such as GaP photo diodes.

The wavelength-converting material may further be encapsulated in order to prevent an impact of the oxygen content onto the analytic measurements. The encapsulation may take place by using an appropriate matrix material, wherein the wavelength-converting material is fully or partially contained in the matrix material, such as dispersed into the matrix material. As an example, one or more resins may be used as a matrix material, such as epoxy resins. The matrix material itself may form the coating. Thus, one or more fluorophores as the wavelength-converting material may be comprised in one or more residents forming a coating of the image sensor chip. Additionally or alternatively, one or more glasses may be used as a matrix material, the glasses containing one or more dopants as wavelength-converting materials. As an example, one or more rare earths may be used as dopants having wavelength-converting properties. These types of glasses containing one or more dopants are known, as an example, from fiber technology. The glasses may be coated directly onto the image sensor chip and/or may be manufactured separately and independently and, subsequently, may be mechanically mounted to the image sensor chip, such as by using one or more glass plates having the appropriate dopants. In this or other ways, an excellent signal-to-noise ratio may be achieved.

The above-mentioned detector in one or more of the disclosed embodiments specifically may be combined with a test chemistry containing NAD. Thus, an excitation wavelength may be chosen closer to the maximum of absorption of NADH, i.e. closer to approximately 350 nm. For a test chemistry with better stability carba-NAD as well as a mutant enzyme may be employed (e.g. as described e.g. in WO 2009/103540 A1 or in WO 2010/094632 A1). Due to the shift in the absorption peak of carba-NADH a light-emitting device or light source, such as an LED, emitting at a wavelength of approximately 365 nm may be preferred. Alternatively, analytical systems containing a detection layer with indicators absorbing in the visible range or infrared may be used, such as 2,18 phosphomolybdate (as e.g. disclosed in EP821234B1) or tetrazolium salts (e.g. as disclosed in U.S. Pat. No. 6,656,697B1 or U.S. Pat. No. 7,867,728B2).

The invention as outlined herein may also be applied to or may be realized by analytical detection layers using oxidative coupling with glucose oxidase/peroxidase and indicators MBTH-ANS or MBTH-DMAB (as described e.g. in U.S. Pat. No. 4,935,346A or EP1167540B1)

By using the wavelength-converting material, such as a fluorescent Europium-containing material, light remitted from the test chemistry, such as in a photometry mode of measurement, may be shifted closer towards the maximum of sensitivity of the pixels of the detector, such as the pixels of a silicon image sensor chip.

The device may further comprise at least one control unit, wherein the at least one control unit is adapted to perform the method according to the present invention, i.e. the method according to one or more of the embodiments disclosed above or disclosed in further detail below. As outlined above, the at least one control unit preferably may comprise one or more processors, wherein the one or more processors may form a computer system and/or a computer and/or a computer network.

Specifically, the control unit may comprise one or more processors which, by implementation of appropriate software and/or program code, are adapted to perform the method according to the present invention. Thus, for further potential details of the device, reference may be made to the method disclosed above and/or disclosed in further detail below.

The device preferably may be a hand-held device and/or portable device. The implementation of the method according to the present invention is specifically advantageous in hand-held devices since the hardware resources required for performing the method according to the present invention may be kept at a rather low level. Thus, low-level data storage systems as well as low-level control units, specifically rather simple processors, may be used, without the necessity of using sophisticated image analysis tools. Specifically, the correction of the relative position change between the image detector and the test field in the image sequence, preferably by using one or more correlation means, may be implemented by using rather low-level processors.

As outlined above, the control unit preferably may comprise at least one processor. The at least one processor preferably may comprise one or more micro-controllers. Additionally or alternatively, the at least one processor may comprise at least one application-specific integrated circuit (ASIC).

In a further aspect of the present invention, a test system for detecting at least one analyte in at least one sample of a body fluid is disclosed. The test system preferably may be a hand-held and/or portable test system. With regard to the expression portable, reference may be made to the definition given above. The test system comprises at least one device according to the present invention, according to one or more of the above-mentioned embodiments and/or according to one or more of the embodiments disclosed in further detail below. Further, the test system comprises at least one test element having at least one test field with at least one test chemistry. With regard to the at least one test element and the at least one test field, reference may be made to the above-mentioned disclosure. The test chemistry is adapted to perform at least one optically detectable detection reaction in the presence of the analyte.

The test system preferably further may comprise at least one puncture element. As used herein, the term puncture element refers to an arbitrary element adapted to create one or more openings in a skin portion of a user. The at least one puncture element may comprise one or more lancets or lancet elements. The test system may further be adapted to puncture at least one skin portion of a user by using the puncture element. Thus, the test system may comprise one or more actuators adapted to engage the at least one puncture element and to drive the puncture element in a forward movement in order to puncture at least one skin portion of the user. Further, the at least one actuator may be adapted to retract the at least one puncture element from the skin portion of the user. Optionally, during this retraction movement, the sample of the body fluid may be gathered by the puncture element and, optionally, may be transferred onto the at least one test element. Thus, the test system may be adapted to puncture at least one skin portion of the user by using the puncture element, thereby creating the sample of the body fluid, wherein the test system may further be adapted to transfer the sample of the body fluid onto the test field of the test element. The sample transfer may be performed in various ways. Thus, at least one transfer element may be performed, and/or the at least one puncture element may be brought in close proximity or in contact with the at least one test field, in order to transfer the sample of the body fluid.

The puncture element preferably may comprise at least one micro-sampler. The at least one micro-sampler may comprise at least one lancet tip and at least one capillary for taking up the sample of the body fluid. Thus, the micro-sampler may comprise one or more lancets having one or more lancet tips, each lancet having at least one capillary, preferably at least one capillary channel or at least two capillary channels. As used herein, the term capillary may comprise any type of element adapted for taking up and/or transporting a liquid by capillary action. The capillary may comprise a closed channel, such as a channel in a hollow needle, and/or an open channel, such as a capillary groove or a capillary slit. The closed channel may circumferentially be enclosed by a tubular capillary wall, whereas the open channel may provide an open surface along a longitudinal axis of the channel.

The sample transfer may be performed in several ways, as outlined above. Thus, the test system may be adapted to press the puncture element, preferably the micro-sampler, onto the test field, thereby at least partially transferring the sample of the body fluid onto the test field. Thus, when using the micro-sampler, the micro-sampler may be pressed onto the test field. Therein, preferably, the optional at least one capillary channel may be brought into contact with the at least one test field. Thus, the body fluid contained in the capillary channel is transferred at least partially onto the test field. Additionally or alternatively, other types of sample transfer may be possible.

The test field preferably may be located inside a cavity of a housing of the test element. One single test field may be comprised or located in one housing, or several test fields may be comprised or located in one housing of the test element. A test element thus may be defined as an element having at least one test field, preferably suited for a single test, i.e. for precisely one detection of an analyte in a sample of a body fluid. One test element or several test elements may be comprised in the test system, such as by using a magazine comprising one test element or a magazine comprising more than one test element. Further, several test elements may share a housing or a housing part, such as by implementing a plurality of cavities, each receiving at least one test field, inside a common housing. Further, as outlined above, at least one puncture element may be located in each cavity. Preferably, the transfer of the body fluid onto the test field may take place inside the cavity.

In a further preferred embodiment, the test system may be adapted to transfer the sample of the body fluid onto the test field from an application side. The image detector preferably may be adapted to acquire the image sequence of images of the test field from a detection side being located oppositely to the application side. Thus, the test element preferably may comprise one or more carriers, wherein the test field is applied to the carrier. The sample of the body fluid may be applied to the test field from the application side. The carrier may be transparent and/or may comprise one or more openings, wherein the acquisition of the image sequence may take place through the carrier, such as by using a transparent carrier and/or through the one or more optional openings inside the carrier.

Further, the test element may comprise one or more housings. A viewing window through which the detection side is observable may be defined by the window provided by the housing of the test element. In this regard, reference may be made to the disk-shaped test element magazine disclosed by WO 2010/094426 A1 as disclosed above. Other embodiments of the test element may be realized.

The test chemistry, as outlined above, preferably may directly or indirectly be applied to a test chemistry carrier of the test element. Further, as outlined above, the test system may comprise a plurality of test elements comprised in a magazine. The magazine preferably may comprise a magazine housing, wherein the test system further comprises a test chemistry carrier, wherein the test chemistry carrier is mechanically connected to the housing, preferably by a form-fit connection and/or by a force-fit connection. As outlined above, this type of connection for connecting the test chemistry carrier to the housing is rather favorable with regard to manufacturing. However, as outlined in the discussion of the prior art above, some relative movements of the test chemistry carrier and the housing are possible during handling of the test system, specifically relative movements of the test field and the window provided by the housing of the test element. The above-mentioned correction of the relative position change, however, may be adapted to correct for these movements, thereby improving the precision and accuracy of the analyte detection.

The magazine generally may have an arbitrary shape. Thus, a magazine comprising precisely one test element may be provided, such as a rectangular magazine. Alternatively, the magazine may comprise a plurality of test elements. Thus, as outlined above, the magazine may have an annular shape. In this case, the test elements preferably are oriented in a radial fashion inside the annular-shaped magazine. Thus, the annular-shaped magazine may comprise a plurality of radially oriented chambers inside a housing of the magazine, wherein, inside each chamber, at least one micro-sampler may be located and wherein, inside each chamber, at least one test field may be located adapted for sample application.

The devices and methods according to the present invention provide a large number of advantages over devices and methods known in the art. Thus, specifically, the method according to the present invention provides the possibility of realizing a dynamic algorithm, which, firstly, corrects for a relative position change. Thus, the test field position and/or the test field rotation may be determined and/or corrected. By correcting for position changes and/or by knowing the test field position and/or test field rotation, all subsequent image processing steps may be performed on the same basis. Ideally, the correction is performed in such a way that the boundaries of the test field and/or the boundaries of a visible window of the test field run horizontally and/or vertically in a coordinate system of the image recognition process. Thus, ideally, search lines may be used in the image processing, which are comparable in all images of the corrected image sequence. Further, by knowing the boundaries of the test field and/or the boundaries of a visible window of the test field, boundary areas of the test elements, such as areas outside the test field and/or portions of the test element outside the test field, which, due to mechanical tolerances, are in the field of view of the image detector, may be eliminated for further image processing.

The method according to the present invention provides means for solving the technical problem of correcting misplacements and/or deformations in an image sequence of a test field during complex operations, which might include application of the sample and detection reactions. Contrarily, the disclosure of EP 2 270 421 A1 deals with the fact that, during monitoring of a test piece in a holder, mechanical displacements may occur due to mechanical tolerances. Consequently, EP 2 270 421 A1 proposes a recognition of a reference mark placed outside the test field (see e.g. par. [0066]) and proposes an upfront correction of the misplacement, before the actual measurement starts (see e.g. par. [0036]). EP 2 270 421 A1, however, does neither recognize the technical problem of image shifts or image the formations during operation and during the detection reaction nor does it provide any technical solutions for this problem.

Further, the method according to the present invention easily allows for determining the moment of application of the sample of the body fluid onto the test field. This moment of sample application may be determined on the basis of the information values stored in the pixels of the corrected images. As outlined above, a touchdown image or corrected touchdown image may be identified in the sequence of images or corrected sequence of images, the touchdown image being the image in the image sequence acquired closest to the moment of sample application. The touchdown image may be used for taking into account changes in the image sequence due to sample application and/or wetting of the test field, which are not generated by the detection reaction itself and which therefore do not contain information relating to the analyte concentration. The touchdown image may be used for precisely determining a region of interest and/or for precisely determining the analyte concentration. Further, one or more threshold values may be used, such as one or more threshold values for detecting a change in the information values averaged over the matrices of the corrected images, indicating a wetting of the test field by the sample of the body fluid.

Further, as outlined above, the method according to the present invention allows for an easy determination of a blank image, preferably an averaged blank image. This determination of the averaged blank image preferably takes place in parallel to the determination of the moment of sample transfer. The determination of the averaged blank image may be performed at a very high precision by using the corrected images of the corrected image sequence before application of the sample of the body fluid, such as before contacting the micro-sampler to the test field. As outlined above, for determining the averaged blank image, a continuous process may be used, which may also be named as a moving process or gliding process. Thereby, in a moving process, a preliminary averaged blank image may be derived from the corrected blank images acquired so far, wherein, with each new acquired blank image, the preliminary averaged blank image may be revised. The averaging may take place on a pixel-by-pixel basis. In other words, the information values such as the gray values stored at a specific coordinate of one image are combined with corresponding information values such as corresponding gray values of other images at the same coordinate. For this combination, basically any type of averaging process may be used, such as a process determining an arithmetic mean value, a geometric mean value or other types of averaging processes.

Specifically the above-mentioned correction of the images allows for a compensation for vibrations and/or shocks of the images, which, in conventional measurements, may lead to a shaking or blurring during the measurements. Thus, in conventional methods, due to these vibrations and shocks, a combination of a plurality of images typically implies a high degree of uncertainty. Contrarily, in the method according to the present invention, a combination of the corrected images of the corrected image sequence on a pixel-by-pixel basis is possible, since the correction allows for a correct combination of corresponding pixels. Thus, the averaged blank image may be derived with a high degree of precision.

Further, the method according to the present invention allows for a significant reduction of image data to be stored in a data storage. Thus, by combining the blank images of the corrected image sequence to one single averaged blank image, a storage of this averaged blank image is fully sufficient for further and subsequent determination of the analyte concentration. Further, the continuous process or moving average process which may be used for determining the averaged blank image is highly resource-efficient, too. Thus, all corrected blank images acquired so far may be combined to the preliminary averaged blank image and, thus, only the preliminary averaged blank image may be stored, whereas the corrected blank images themselves may be erased.

Further, the above-mentioned correction of the relative position change may be performed in a rather simple and resource-efficient manner which easily may be implied even in hand-held or portable devices. Thus, the correction may take place on the basis of a pattern recognition using the at least one characteristic feature of the image sequence. The characteristic feature preferably may be or may comprise an image section of the images of the image sequence having a defined position and size, such as an image section in a reference image of the image sequence. As a reference image, for example, the first image of the image sequence may be chosen. For the purpose of the above-mentioned correction, the degree of identity or match of this image sequence with image sequences in another image may be quantified. This quantification may easily be embodied by appropriate algorithms. Thus, the degree of identity or the match may be quantified by using cross correlations or cross correlation coefficients, preferably normalized cross correlation coefficients. Further, a displacement in the images to be compared may be used, such as an Euclidean distance. In this way and/or in other ways, such as by varying the Euclidian distance, the images to be compared may virtually be shifted and/or rotated relative to each other by varying degrees, wherein, for each variation, the degree of identity and/or the match may be determined, such as the pattern match of the image section with the corresponding image section in the image to be compared. The shift and/or rotation leading to the highest degree of identity and/or to the highest match may be used for a correction of the images, such as for transforming the matrices.

Further, optionally, the degree of identity or match may be compared with one or more thresholds or limit values. Thus, in case the degree of identity and/or match should be found to be below a predetermined limit value, a different type of characteristic feature, such as a different image section of the reference image, may be used, and the process of pattern matching may be repeated. Thus, a different image section having a different position and/or a different size may be used for a new trial.

The method of recognizing the characteristic feature for the purpose of correction implies a number of advantages as compared to other methods known in the art. Thus, as an example, brightness variations in between the images and/or minor errors or faults in the images, such as faults due to impurities and dirt of the detector and/or an optical system and/or the test chemistry, typically do not lead to a failure of the pattern recognition. Not until the faults or errors lead to significant disruptions or disturbances of the image, which should lead to a detection of an error anyway, the method will fail due to insufficient degrees of identity. Thus, the method may even be used for determining errors in image acquisition, thereby leading to a selection and discarding of faulty images, or even to an abortion of the measurement at all, optionally in conjunction with an appropriate warning provided to a user of the device.

Further, by using the method according to the present invention, the region of interest may be determined rather efficiently, even for complex geometries of the test field and/or for complex geometries of the sample transfer onto the test field, such as a sample transfer via one or more capillaries. Thus, even complex geometries of sample transfer onto the test field may be processed, leading to regions of interest having a rather irregular shape. As an example, micro-samplers having one, two or more capillary channels may be used, wherein the sample transfer from these capillary channels onto the test field leads to an irregular shape of the area to which the sample of the body fluid is applied. Thus, the region of interest may be determined by detecting significant changes in the corrected sequence of images. For this purpose, one or more corrected images of the corrected image sequence after the moment of sample application to the test field, such as images acquired at a predetermined waiting time (also referred to as a predetermined time span) after the moment of sample transfer or sample application (such as waiting times of 1 s or similar waiting times), may be evaluated, preferably on a pixel-by-pixel basis, and significant changes may be detected. The significant changes, as outlined above, may be determined by comparing this corrected image acquired after the moment of the sample application to an image acquired before or after sample application, such as the touchdown image. In case the image quality of the corrected image acquired after the moment of sample application, such as a signal-to-noise-ratio, should be insufficient, one or more further corrected images acquired after the moment of sample application may be used for detecting significant changes, such as by averaging a plurality of corrected images acquired after the moment of sample application. Thus, one or more of the corrected images acquired after sample application may be used for generating an averaged corrected image after sample application, and difference values or one or more comparison matrices may be determined. Thus, the averaged image after sample application may be compared to the averaged image acquired before or during sample application, thereby creating one or more averaged difference matrices, such as by determining differences of these matrices on a pixel-by-pixel basis. Thus, the difference matrix may comprise, in each field, difference values of the corresponding information values of the averaged corrected image matrix acquired after sample application and the image acquired before or during sample application.

By using these or other types of comparison, the significant changes may easily be evaluated, such as by using histograms and/or one or more threshold methods. Further, optionally, a filtering of the histograms and/or an averaging of the histograms may be performed. On the basis of the at least one histogram, a threshold value may be determined, which may be used for evaluating the significant changes, such as for evaluating the data contained in the difference matrix.

As outlined above, the region of interest generally may contain a set of coordinates in the corrected images, i.e. a group of pixels in each corrected image which may be used for qualitatively and/or quantitatively determining the analyte in the sample of the body fluid, such as for determining the concentration of the at least one analyte. By using the method according to the present invention and by using the possibility of averaging a plurality of images for detecting significant changes in the images, the determination of the region of interest may be kept rather efficient and simple. Thus, since all corrected images are comparable with regard to their positioning and/or rotation, borderlines of the region of interest may be determined, which may be applicable to a plurality of corrected images or even to all corrected images.

Thus, in a next step for determining the region of interest, horizontal and/or vertical averages in the corrected images may be determined in the difference matrix, such as in an x-direction and/or a y-direction of the difference matrix containing the difference values. Thus, a maximum of averaged gray values in the difference matrix may be calculated, for one or more directions in space, such as a maximum for an x-direction (horizontal direction of the corrected images) and/or a maximum of a y-direction (vertical direction of the corrected images). On the basis of this at least one maximum, at least one threshold value may be determined, such as at least one threshold value for each direction in space. By using this at least one threshold value, significant changes may be determined, such as significant changes in the horizontal and/or vertical mean values. Thereby, the borderlines of the region of interest in the difference matrix may be determined, i.e. the coordinates of the borderlines indicating the position of the borderlines in this matrix. Additionally and optionally, safety distances may be applied and/or the known geometry of the sample transfer, such as the geometry of the micro-sampler, may be used for correcting this region of interest. Generally, by using the difference matrix indicating changes before and after sample application on a pixel-by-pixel basis, borderlines of the region of interest may be determined, such as four borderlines for a rectangular region of interest, in order to roughly delimit the region of interest.

This determination of the region of interest may further be refined by further processing of the information values of pixels within the roughly determined region of interest. Thus, generally, the determination of the region of interest may comprise several steps, such as at least one rough determination of the region of interest and at least one refined determination of the region of interest. Thus, as soon as a rough estimation of the region of interest is known, such as by determining borderlines of the region of interest, such as borderlines defining one or more rectangular regions of interest, this rough estimation of the region of interest may further be evaluated by statistical methods. Thereby, an additional discarding of one or more regions within these rough borderlines may be performed. As an example, the rough region of interest may further be evaluated by using one or more histograms and/or by using one or more filtering steps, such as filtering steps for filtering the histogram, in order to search significant pixels, i.e. pixels to be assigned to the refined or revised region of interest. Thus, on the basis of a histogram and/or filtered histogram of information values of pixels of the difference matrix inside the rough region of interest, one or more threshold values may be determined. Information values of pixels on one side of the threshold values may be assigned to the region of interest, whereas pixels on the other side of the threshold may be determined to be outside the region of interest. Additionally or alternatively, for finding the at least one threshold, the above-mentioned Otsu method may be used, which may be based on normalized histograms.

In this way or another way, by evaluating significant changes of the corrected images before/during sample application and after sample application, the region of interest may easily be determined as a set or group of coordinates or positions within the corrected images. Thus, the region of interest may easily be represented by a binary matrix indicating whether a pixel of the corrected images belongs to the region of interest or not. This binary mask or binary matrix on a pixel-by-pixel basis may precisely define the region of interest even for complex geometries of the micro-samplers, as opposed to traditional methods which, typically, make use of definitions of regions of interest by rather simple geometries, such as circular geometries and/or rectangular geometries.

On the basis of this precisely defined region of interest, preferably containing a binary mask and/or a precise definition of pixel coordinates of pixels belonging to the region of interest, a precise evaluation of the corrected images may be performed, in order to qualitatively and/or quantitatively detect the at least one analyte, such as for determining the analyte concentration at a high degree of precision. Thus, by evaluating the information values of the pixels within the region of interest in the corrected images, the reaction kinetics of the detection reaction may be evaluated, preferably on a pixel-by-pixel basis and/or on an averaged basis, in order to determine the analyte concentration. For this purpose of determination of the analyte concentration, one or more evaluation algorithms may be used, which may be predetermined and/or determinable. As outlined above, it is even possible to choose an appropriate evaluation algorithm on the basis of changes in the information values after a start of the detection reaction, such as by comparing information values of one or more images acquired before or during sample application and one or more images acquired at a predetermined time span a waiting time after sample application, such as 1 second after sample application.

For the purpose of determination of analyte concentration, generally, the information values in these corrected images acquired after the moment of sample application may be corrected and/or normalized, such as by normalization on a pixel-by-pixel basis by using the averaged blank image. Thereby, from each corrected image of the corrected image sequence acquired after the moment of sample application, corresponding matrices containing, as an example, relative remission values for each pixel may be determined, such as by dividing the information value of each pixel by the corresponding information value contained in the corresponding pixel of the averaged blank image and/or by subtracting offsets on a pixel-by-pixel basis. Based on these corrected and/or modified images, an averaging of the pixels of the corrected images may take place, thereby obtaining a very precise averaged value of the information values of the pixels within the region of interest.

Summarizing the above-mentioned findings and optional embodiments of the present invention, the following embodiments of the present invention are preferred:

Embodiment 1

A method for detecting at least one analyte in at least one sample of a body fluid, preferably for detecting glucose in blood and/or interstitial fluid, wherein at least one test element with at least one test field is used, the at least one test field having at least one test chemistry, wherein the test chemistry is adapted to perform at least one optically detectable detection reaction in the presence of the analyte, preferably a color changing reaction, wherein the method comprises acquiring an image sequence of images of the test field by using at least one image detector, wherein each image comprises a plurality of pixels, wherein the method further comprises detecting at least one characteristic feature of the test field in the images of the image sequence, wherein the method further comprises correcting a relative position change between the image detector and the test field in the image sequence by using the characteristic feature, thereby obtaining a sequence of corrected images.

Embodiment 2

The method according to the preceding embodiment, wherein each image of the sequence of images contains a matrix of information values, preferably a matrix of gray values.

Embodiment 3

The method according to one of the preceding embodiments, wherein the correction of the relative position change between the image detector and the test field comprises at least one correction selected from the group consisting of: a correction of a translation of an image of the test field on the image detector in at least one spatial direction; a correction of a rotation of an image of the test field on the image detector about at least one rotational axis; a correction of a distortion of an image of the test field on the image detector, preferably a distortion due to a warpage of the test field.

Embodiment 4

The method according to one of the preceding embodiments, wherein the images of the image sequence are acquired in a constant time sequence and/or at a constant frame rate.

Embodiment 5

The method according to one of the preceding embodiments, wherein the image detector comprises at least one detector selected from the group consisting of a line detector and a two-dimensional detector.

Embodiment 6

The method according to one of the preceding embodiments, wherein the correction of the relative position change comprises using at least one image of the image sequence as a reference image, wherein the reference image is kept unchanged, wherein the remaining images of the image sequence are corrected by using at least one calculational correction of the position of the pixels, wherein the calculational correction is chosen such that a correlation between the reference image and the corrected remaining images of the image sequence is maximized.

Embodiment 7

The method according to the preceding embodiment, wherein the calculational correction comprises a shifting of the pixels of the remaining images of the image sequence in at least one spatial direction, wherein the shifting is chosen such that the correlation between the reference image and the corrected remaining images is maximized.

Embodiment 8

The method according to the preceding embodiment, wherein the shifting is individually chosen for each image of the remaining images of the image sequence.

Embodiment 9

The method according to one of the three preceding embodiments, wherein the calculational correction comprises at least one rotation of the remaining images of the image sequence about at least one rotational axis by at least one rotation angle, wherein the rotational axis and/or the rotation angle are chosen such that the correlation between the reference image and the corrected remaining images is maximized.

Embodiment 10

The method according to the preceding embodiment, wherein the rotational axis and/or the rotation angle are individually chosen for each image of the remaining images of the image sequence.

Embodiment 11

The method according to one of the preceding embodiments, wherein the characteristic feature comprises at least one feature selected from the group consisting of: a roughness of the test field detectable in the images of the image sequence; a granularity of the test chemistry of the test field detectable in the images of the image sequence; faults of the test field detectable in the images of the image sequence; at least one, preferably at least two, fiducial marks comprised in the test field and detectable in the images of the image sequence.

Embodiment 12

The method according to one of the preceding embodiments, wherein a concentration of the analyte is detected by detecting at least one optical property of the test chemistry and/or by detecting at least one change of at least one optical property of the test chemistry due to the optically detectable detection reaction.

Embodiment 13

The method according to the preceding embodiment, wherein the at least one optical property comprises at least one of a color, an absolute remission, a relative remission and a fluorescence.

Embodiment 14

The method according to one of the preceding embodiments, wherein the sample of the body fluid is applied to the test field during acquisition of the image sequence.

Embodiment 15

The method according to the preceding embodiment, wherein the image sequence comprises a blank image sequence, wherein the blank image sequence comprises a plurality of blank images acquired before applying the sample of the body fluid to the test field.

Embodiment 16

The method according to the preceding embodiment, wherein at least one averaged blank image is derived from the blank images of the blank image sequence after performing the correction of the relative position change of the blank images of the blank image sequence.

Embodiment 17

The method according to the preceding embodiment, wherein the averaged blank image is derived in a continuous process during acquiring the images of the image sequence, wherein a preliminary averaged blank image is derived from the corrected blank images acquired so far, wherein new acquired blank images are used for revising the preliminary averaged blank image.

Embodiment 18

The method according to one of the two preceding embodiments, wherein information of corresponding pixels of the corrected blank images of the blank image sequence are used for deriving an information of a corresponding pixel of the averaged blank image.

Embodiment 19

The method according to the preceding embodiment, wherein the information of corresponding pixels of the corrected blank images are combined by at least one linear combination and/or by at least one averaging operation for deriving the corresponding pixel of the averaged blank image.

Embodiment 20

The method according to one of the five preceding embodiments, wherein the analyte is detected by comparing the images of the sequence of corrected images with the blank image sequence, preferably with the averaged blank image.

Embodiment 21

The method according to the preceding embodiment, wherein the comparison is performed on a pixel-by-pixel basis.

Embodiment 22

The method according to the preceding embodiment, wherein the information contained in each pixel of the images of the sequence of corrected images after application of the sample of the body fluid to the test field is divided by the information contained in the corresponding pixel of at least one blank image, preferably the averaged blank image, thereby creating a normalized information for each pixel, wherein, preferably, a sequence of corrected relative images is created, each corrected relative image having pixels containing the normalized information of the respective pixel.

Embodiment 23

The method according to the preceding embodiment, wherein at least one averaged normalized value is created over at least part of the sequence of corrected relative images, preferably over a region of interest of the corrected relative images.

Embodiment 24

The method according to the preceding embodiment, wherein the normalized value is an average value over the part of the sequence of the corrected relative images, preferably over the region of interest of the corrected relative images.

Embodiment 25

The method according to one of the two preceding embodiments, wherein the averaged normalized value is used for deriving a concentration of the analyte in the body fluid.

Embodiment 26

The method according to one of the three preceding embodiments, wherein the averaged normalized value is monitored as a function of time after application of the sample of the body fluid to the test field, thereby preferably generating a kinetics curve.

Embodiment 27

The method according to one of the preceding embodiments, wherein boundaries of the test field and/or boundaries of a visible window of the test field are detected in the sequence of corrected images, preferably in the corrected blank image sequence and/or in the averaged blank image.

Embodiment 28

The method according to the preceding embodiment, wherein the boundaries are detected by using a threshold method and/or a pattern recognition method.

Embodiment 29

The method according to one of the preceding embodiments, wherein a moment of application of the sample of the body fluid onto the test field is detected in the image sequence.

Embodiment 30

The method according to the preceding embodiment, wherein the moment of application of the sample of the body fluid onto the test field is detected by observing changes of the information contained in the image sequence.

Embodiment 31

The method according to the preceding embodiment, wherein changes of averaged information contained in the images of the image sequence are observed.

Embodiment 32

The method according to one of the three preceding embodiments, wherein the moment of application of the sample of the body fluid onto the test field is detected by observing changes in the corrected images of the corrected image sequence.

Embodiment 33

The method according to one of the four preceding embodiments, wherein neighboring averaged images of the image sequence are compared after correction obtaining a difference averaged value for each pair of neighboring images, wherein the moment of application of the sample onto the test field is detected by comparing the difference averaged value with at least one threshold.

Embodiment 34

The method according to one of the preceding embodiments, wherein the sample of the body fluid is applied to the test field during acquisition of the image sequence, wherein at least one touchdown image, preferably at least one corrected touchdown image, is detected in the image sequence, preferably the corrected image sequence, wherein the touchdown image is an image of the image sequence acquired at a point in time closest to the moment of application of the sample of the body fluid onto the test field.

Embodiment 35

The method according to the preceding embodiment, wherein the analyte is detected by comparing the images of the sequence of corrected images with the touchdown image.

Embodiment 36

The method according to the preceding embodiment, wherein the comparison is performed on a pixel-by-pixel basis.

Embodiment 37

The method according to one of the preceding embodiments, wherein after application of the sample of the body fluid onto the test field at least one region of interest is determined in the image sequence.

Embodiment 38

The method according to the preceding embodiment, wherein at least one corrected image acquired before or during application of the sample of the body fluid onto the test field is compared to at least one corrected image acquired after application of the sample of the body fluid onto the test field on a pixel-by-pixel basis.

Embodiment 39

The method according to the preceding embodiment, wherein a difference value is generated for each pixel, wherein the difference value denotes a difference of the information contained in corresponding pixels of the corrected images acquired before or during application of the sample of the body fluid onto the test field and after application of the sample of the body fluid onto the test field, wherein the pixels are classified as pixels belonging to the region of interest or as pixels not belonging to the region of interest based on the difference values.

Embodiment 39

The method according to the preceding embodiment, wherein at least one threshold method is used for classifying the pixels, preferably an Otsu method.

Embodiment 40

The method according to one of the three preceding embodiments, wherein an image mask is generated denoting the pixels belonging to the region of interest.

Embodiment 41

The method according to the preceding embodiment, wherein the image mask is a binary mask.

Embodiment 43

The method according to one of the six preceding embodiments, wherein only pixels belonging to the region of interest in the sequence of corrected images are used for detecting the analyte in the sample of the body fluid.

Embodiment 44

A computer program comprising program means for executing the method steps of the method according to one of the preceding embodiments when the computer program is executed on a computer or a computer network.

Embodiment 45

The computer program according to the preceding embodiment, wherein the program means are stored on a storage medium readable by a computer or computer network.

Embodiment 46

A computer system having at least one processor for loading the computer program according to one of the two preceding embodiments and for executing the computer program.

Embodiments 47

A storage medium, wherein a data structure is stored on the storage medium, wherein the data structure is adapted to perform the method according to one of the preceding embodiments referring to a method, after having been loaded into a computer or computer network.

Embodiment 48

A device for detecting at least one analyte in at least one sample of a body fluid, wherein the device comprises at least one test element receptacle for receiving at least one test element having at least one test field with at least one test chemistry, wherein the device further comprises at least one image detector for acquiring an image sequence of images of the test field, wherein the device further comprises at least one control unit, wherein the control unit is adapted to perform the method according to one of the preceding embodiments.

Embodiment 49

The device according to the preceding embodiment, wherein the device is a hand-held and/or portable device.

Embodiment 50

The device according to one of the two preceding embodiments, wherein the image detector comprises at least one of a line detector and a two-dimensional image detector, preferably one of a CCD line sensor, a CMOS line sensor, a two-dimensional CCD array sensor and a two-dimensional CMOS array sensor.

Embodiment 51

The device according to one of the preceding embodiments referring to a device, wherein the control unit comprises at least one processor.

Embodiment 52

A test system for detecting at least one analyte in at least one sample of a body fluid, the test system comprising at least one device according to one of the preceding embodiments referring to a device, the test system further comprising at least one test element having at least one test field with at least one test chemistry, wherein the test chemistry is adapted to perform at least one optically detectable detection reaction in the presence of the analyte.

Embodiment 54

The test system according to the preceding embodiment, wherein the test system is a portable test system and/or a handheld test system.

Embodiment 55

The test system according to one of the two preceding embodiments, wherein the test system, preferably the test element, further comprises at least one puncture element, wherein the test system is adapted to puncture at least one skin portion of a user by using the puncture element, thereby creating the sample of the body fluid, wherein the test system is further adapted to transfer the sample of the body fluid onto the test field of the test element.

Embodiment 56

The test system according to the preceding embodiment, wherein the puncture element comprises at least one micro-sampler, the micro-sampler comprising at least one lancet tip and at least one capillary for taking up the sample of the body fluid, preferably at least one capillary channel or at least two capillary channels.

Embodiment 57

The test system according to one of the two preceding embodiments, wherein the test system is adapted to press the puncture element onto the test field, thereby transferring the sample of the body fluid onto the test field.

Embodiment 58

The test system according to one of the three preceding embodiments, wherein the test field is located inside a cavity of a housing of the test element, wherein the transfer of the body fluid onto the test field takes place inside the cavity.

Embodiment 59

The test system according to one of the preceding embodiments referring to a test system, wherein the test system is adapted to transfer the sample of the body fluid onto the test field from an application side, wherein the image detector is adapted to acquire the image sequence of images of the test field from a detection side being located oppositely to the application side.

Embodiment 60

The test system according to the preceding embodiment, wherein a viewing window through which the detection side is observable is defined by a window provided by a housing of the test element.

Embodiment 61

The test system according to one of the two preceding embodiments, wherein the test chemistry is applied to a test chemistry carrier.

Embodiment 62

The test system according to one of the preceding embodiments referring to a test system, wherein the test system comprises a plurality of test elements comprised in a magazine.

Embodiment 63

The test system according to the preceding embodiment, wherein the magazine comprises a magazine housing, wherein the test system further comprises a test chemistry carrier, wherein the test chemistry carrier is mechanically connected to the housing, preferably by a form-fit connection and/or a force-fit connection.

Embodiment 64

The test system according to one of the two preceding embodiments, wherein the magazine has an annular shape, wherein the test elements are oriented in a radial fashion inside the magazine.

These and other features and advantages of the present invention will be more fully understood from the following detailed description of the embodiments taken together with the accompanying claims. It is noted that the scope of the claims is defined by the recitations therein and not by the specific discussion of features and advantages set forth in the present description.

BRIEF DESCRIPTION OF THE DRAWING FIGURES

Further optional details and optional features of the present invention may be derived from the subsequent description of preferred embodiments, preferably in conjunction with the dependent claims. In these embodiments, in each case, the optional features may be realized in an isolated way or in an arbitrary combination of several features. The invention is not restricted to the embodiments. The embodiments are schematically depicted in the figures. Identical reference numbers in the figures refer to identical, similar or functionally identical elements.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE EMBODIMENTS

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Figure 1:
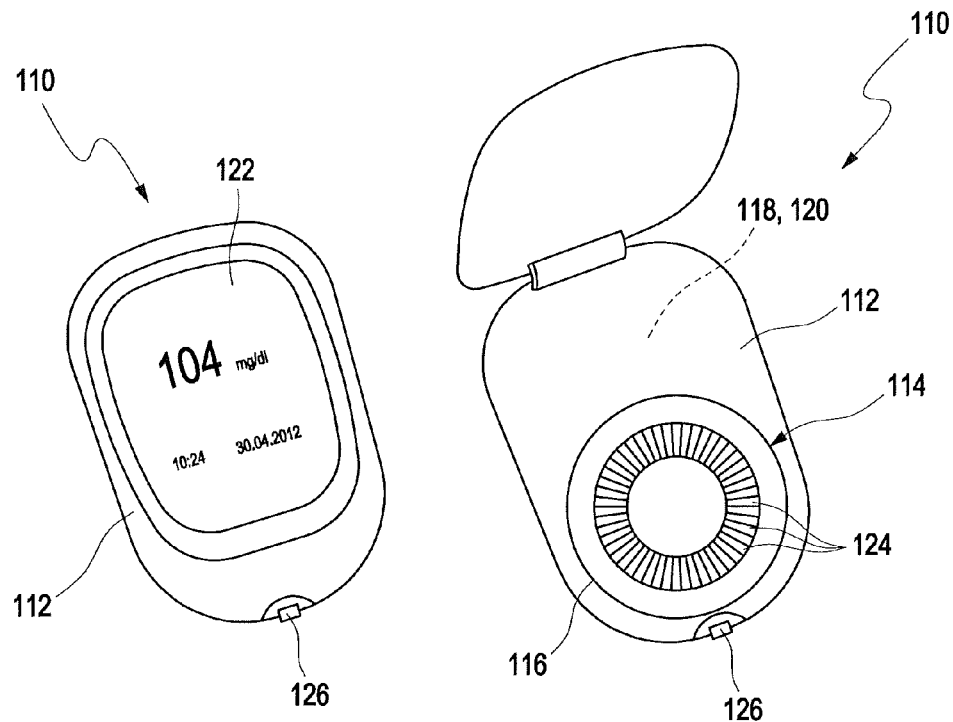
FIG. 1 shows a concept of a device and a test system for detecting an analyte in a sample of a body fluid.

In FIG. 1, a potential test system 110 for detecting at least one analyte in at least one sample of a body fluid is disclosed in two different states, wherein the test system 110 on the left hand side in FIG. 1 is shown in a closed state, and on the right hand side in an opened state. The test system 110 comprises a device 112 for detecting at least one analyte in at least one sample of a body fluid and, as an example, a magazine 114 received in a receptacle 116 of the device 112.

The device 112 may comprise one or more control units, which, in FIG. 1, are generally denoted by reference number 118. Thus, as outlined above, the at least one control unit 118 may comprise at least one processor 120, such as at least one micro-controller. Further, the device 112 may comprise one or more user interfaces 122, such as at least one display and/or at least one operating element allowing for a user to operate the test system 110 and/or the device 112.

In the present embodiment, the magazine 114 comprises a plurality of test elements 124, received in the magazine 114 in a radial fashion, thereby providing an annular shape of the magazine 114 and/or a disk-shape of the magazine 114. It shall be noted, however, that other types of magazines 114 are possible and/or devices 112 using only one test element 124 rather than a plurality of test elements 124.

The device 112 provides at least one application position 126. The device 112 is adapted to rotate the magazine 114 inside the receptacle 116 and to perform a test with the test element 124 located in the application position 126.

Exemplary embodiments of the magazine 114 and/or the test elements 124 are disclosed in various views and details in FIGS. 3A to 3C and FIG. 4. The general setup of these magazines 114 is known e.g. from WO 2010/094426 A1, so reference may be made to this document. However, other setups are possible.

Thus, the magazine 114 may comprise a magazine housing 128, which may also form part of housings 130 of the test elements 124. In this specific embodiment, the housing 130 comprises a lower shell 132, also referred to as the bottom part, which, typically, is made of an intransparent and preferably black plastics material. Further, the housing 130 comprises an upper shell 134, also referred to as the cover part, which, typically, is made of a transparent plastics material. Further, the housing 130 may comprise a sealing film 136, which typically is made of a metal foil, such as an aluminum foil, which may be glued to the upper shell 134 by an adhesive 138.

Further, in this specific embodiment, each test element 124 may comprise one or more skin-piercing or puncture elements 140, which, as an example, may be formed as micro-samplers 142, each micro-sampler containing a lancet 144 with a lancet tip 146 and at least one capillary element, such as at least one capillary channel 148. Further potential details with regard to the micro-samplers 142 will be outlined below.

Further, the magazine 114 may comprise a test chemistry ring 150 comprising a test chemistry carrier 152 and a test chemistry 154 applied to the test chemistry carrier 152 on a side facing the lower shell 132. The test chemistry ring 150 may be glued to the lower shell 132 by at least one adhesive 156, such as an adhesive tape, and/or maybe fixed to the magazine housing 128 by other means.

Figure 4:
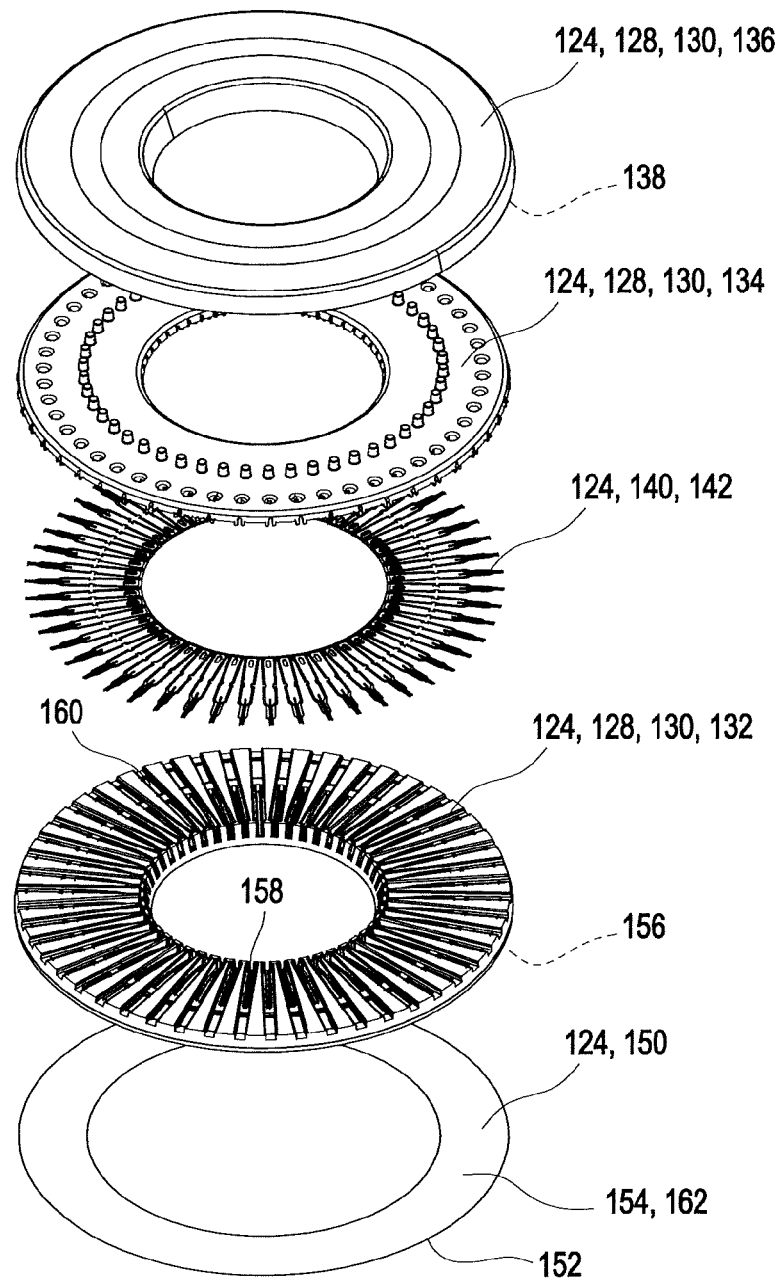
FIG. 4 shows a magazine to be used in the test system according to FIG. 1.

Inside the magazine housing 128, a plurality of cavities 158 is formed, by appropriate recessions in the lower shell 132 and/or the upper shell 134. These cavities 158 may generally be oriented in a radial fashion, as depicted in FIG. 4. In each cavity 158, one micro-sampler 142 is received, with the lancet tip 146 facing to the outer side of the annular-shaped magazine 114 and with the capillary channels 148 facing downward in FIG. 4, towards the test chemistry ring 150.

In each cavity 158, further, a window 160 is formed in the lower shell 132. The test chemistry 154 accessible through these windows 160 thereby forms a test field 162 or part of a test field 162 for each test element 124. Thus, through the window 160, the sample of the body fluid may be applied to the test fields 162. Each test element 124 therefore, in the present embodiment, comprises at least one test field 162 and, optionally, a cavity 158, a puncture element 140 as well as a housing 130, which, in this embodiment, may be an integral part of the magazine housing 128.

Figure 3:
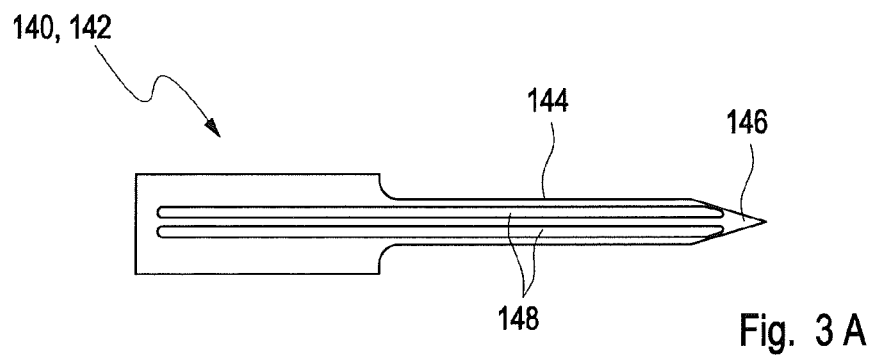
FIGS. 3A to 3C show different views of a micro-sampler which may be used in the test system according to FIG. 1.
Figure 3:
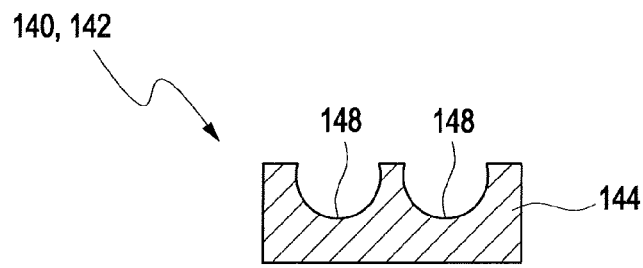
Figure 3:
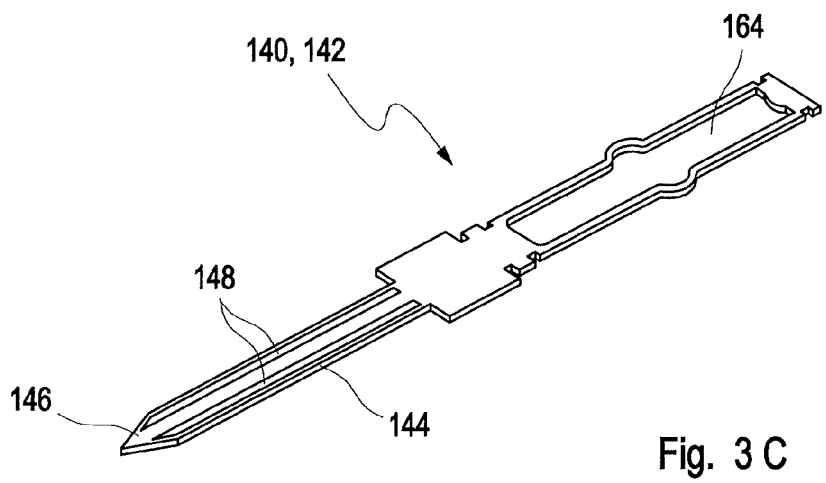

Further details of the sample generation and/or sample transfer will be explained with respect to FIGS. 3A to 3C and FIGS. 5A to 5C. Thus, FIG. 3A shows a top-view of the micro-sampler 142 as disclosed above. FIG. 3B shows a cross-sectional view of the lancet 144 of the micro-sampler 142, showing the at least one, in this embodiment two, capillary channels 148, which, as an example, may have a U-shape. FIG. 3C shows a perspective view of the micro-sampler 142 of FIG. 3A, which further shows an optional engagement opening 164 at a rear end of the micro-sampler 142, which allows for an engagement of the micro-sampler 142 by an actuator of the device 112. This step is schematically depicted in FIGS. 5A and 5B, which show a cross-sectional view of a cavity 158 of a test element 124.

Figure 5:
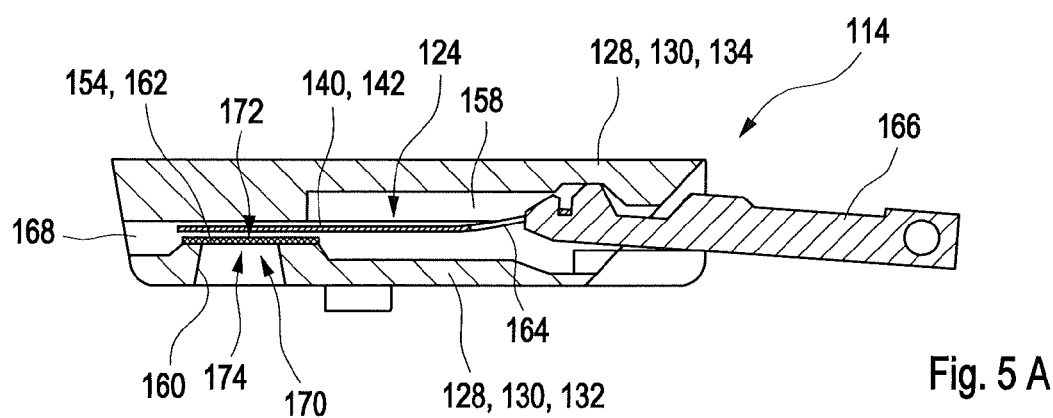
FIGS. 5A to 5C show a schematic view of a sample transfer onto a test field and an image acquisition.
Figure 5:
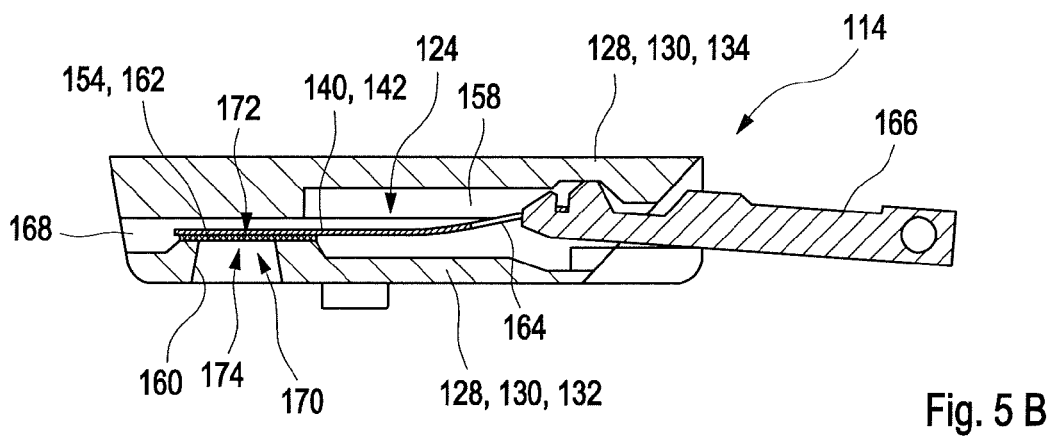
Figure 5:
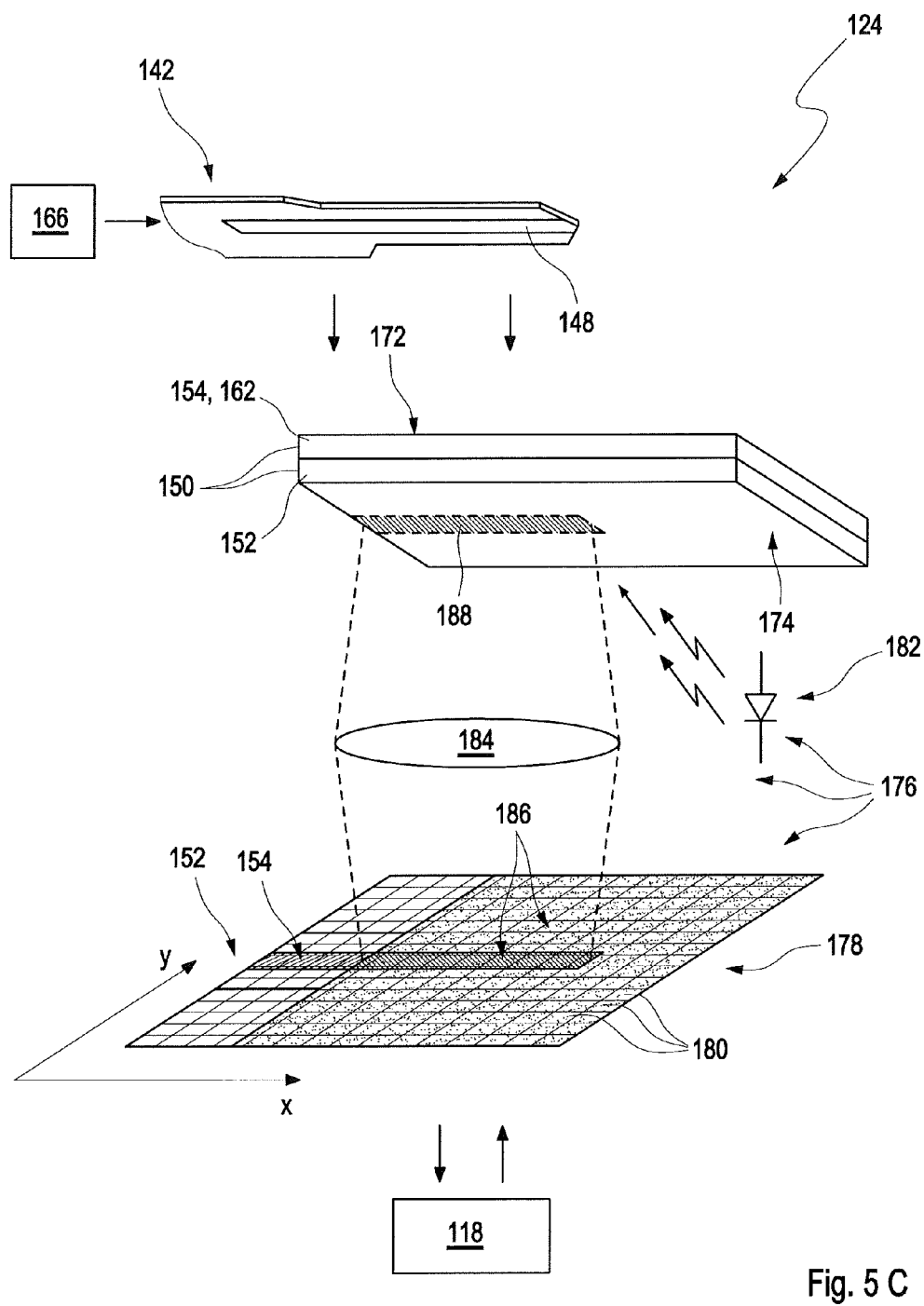

As can be seen in FIG. 5A, an actuator 166 engages a rear end of the micro-sampler 142 and the engagement opening 164, driving the micro-sampler 142 through a puncture opening 168 in the housing 130, when the test element 124 is located in the application position 126 of the device 112, thereby creating an opening in a skin portion of a user and generating and collecting a sample of the body fluid in the capillary channels 148. Afterwards, as depicted in FIG. 5B, the actuator 166 retracts the micro-sampler 142 into the cavity 158, wherein the capillary channels 148, by appropriate curvature of the micro-sampler 142, are pressed against the test field 162. Thereby, at least part of the sample of the body fluid contained in the capillary channels 148 of the micro-sampler 142 is transferred onto the test field 162 of the respective test element 124. Thus, the sample or part of the sample may react with the test chemistry 154 contained in the test field 162 in a detection reaction, which leads to an optically detectable change. This change of at least one optically detectable property of the test chemistry 154 due to the detection reaction may be observed through the window 160, which, thereby, defines a viewing window 170. Thus, the side of the test field 162 facing towards the cavity 158 may form an application side 172, whereas the side facing towards the window 160 may form a detection side 174 of the test field 162 and/or the test element 124. The optically detectable changes may be detected by a detector through the window 160, which is not depicted in FIGS. 5A and 5B.

In FIG. 5C, the process of sample transfer and the detection of the detection reaction by a detector 176 is depicted schematically. The detector 176 comprises an image detector 178 having, as an exemplary embodiment, a rectangular two-dimensional array of photosensitive elements 180, which, in the following, are also referred to as pixels of the image detector 178. Further, the detector 176 may comprise one or more light sources 182, such as one or more light-emitting diode, for illuminating the detection side 174 of the test field 162, for example through the test chemistry carrier 152 of the test chemistry ring 150.

As an example, the light sources 182 may comprise one or more light-emitting diodes (LEDs), such as two light-emitting diodes, emitting in an ultraviolet or blue spectral range, such as in a spectral range of 350 to 400 nm, preferably in a spectral range of 350 to 380 nm or 360 to 365 nm. Alternatively or additionally, other commercially available LEDs, such as Green-LEDs (570+/−30 nm); Red-LEDs (650+/−50 nm) or IR-LEDs (700-1000 nm) may be employed. Additionally or alternatively to LEDs, one or more other types of light sources may be employed. Thus, as an example, light bulbs may be applied. Additionally or alternatively, typically depending on the requirements for the light signal, laser diodes may be used, even though this type of light sources typically implies increased costs.

The detector 176 may further comprise one or more optical elements 184, such as one or more imaging optics, in order to image the test field 162 and/or at least one portion thereof onto the image detector 178, thereby creating an image 186 of the test field 162 and/or a part thereof on the image detector 178. The image 186 may comprise a matrix of information values, such as gray values, forming a matrix in one or two dimensions. In FIG. 5C, a two-dimensional matrix with an x-dimension and a y-dimension is depicted.

For the purpose of the sample transfer, as outlined above with regard to FIGS. 5A and 5B, the micro-sampler 142 is actuated by the at least one actuator 166. When retracting the micro-sampler 142 into the cavity 158 (not depicted in FIG. 5C), as outlined above, the sample contained in the at least one capillary channel 148 of the micro-sampler 142 is transferred onto the test field 162 from the application side 172. This wetting of the test field 162 by the sample of the body fluid as well as optically detectable changes in the test chemistry 154 due to a detection reaction are inhomogeneous, since, typically, only a portion 188 of the test field 162 will be wetted by the sample. By using the control unit 118, a sequence of images 186 may be acquired, in order to be evaluated as outlined in further detail below.

Figure 2:
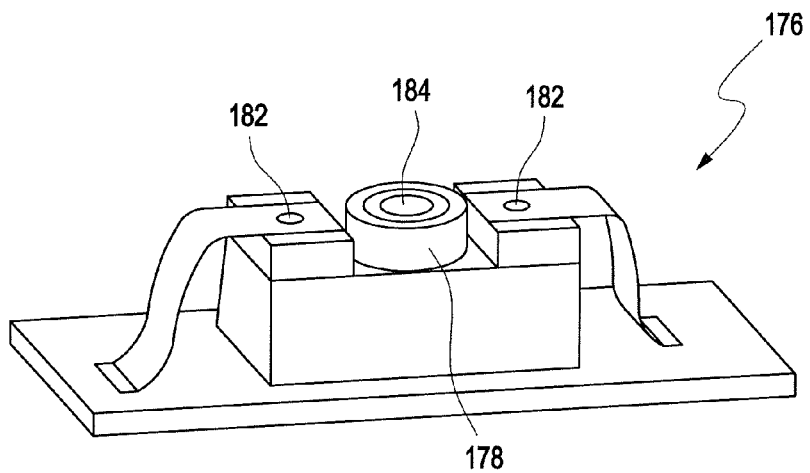
FIG. 2 shows a detector to be used in the test system according to FIG. 1.

In FIG. 2, a perspective view of a potential embodiment of the detector 176 is depicted. As can be seen in this figure, the detector 176, besides the image detector 178 (such as a CCD and/or CMOS detector) and the at least one optical element 184, such as at least one lens, may comprise the at least one light source 182. In this embodiment, two light sources 182 are connected to the image detector 178, thereby forming a detector blog comprising the image detector 178, the light sources 182 and the optical element 184. As schematically depicted in FIG. 5C, preferably, an illumination of the test field 162 and an imaging of the test field 162 by the image detector 178 preferably take place in a non-reflected and/or undirected way, such as by using different angles for illumination and detection. Thus, scattered and/or diffusely reflected light from the test field 162 may be registered by the image detector 178.

As an example, CCD/CMOS image detectors 178 may be used, such as image sensors available from Eureca Messtechnik GmbH, Germany. Thus, image detectors of various manufacturers may be employed, such as CCD/CMOS image detectors manufactured by Fairchild imaging, Panavision, NEC, Sony, Toshiba, CMOS Sensor Inc., Kodak, Texas Instruments, TAOS or others. As an example, CCD/CMOS line sensors and/or areas sensors of one or more of models CCD111A, CCD424 manufactured by Fairchild imaging, of one or more of models LIS-500 or MDIC-2.0 manufactured by Panavision, of model µPD3753CY-A manufactured by NEC, of one or more of models ICX207AK-E or ILX551B manufactured by Sony, of one or more types TCD1201DG or TCD132TG manufactured by Toshiba, of one or more of models M106-A9 or C106 manufactured by CMOS Sensor Inc., of one or more of models KAC9618 or KAC-01301 manufactured by Kodak, of model TC237B manufactured by Texas Instruments or of model TSL201R manufactured by TAOS may be used.

Additionally or alternatively, camera boards containing one or more image sensor chips on printed circuit boards may be used as image detectors 178.

As discussed in further detail above, the detector 176 may further comprise at least one wavelength-converting material, which is not depicted in the figures. Thus, the image detector 178 may be coated with one or more coatings comprising at least one wavelength-converting material such as at least one fluorescent material. Thus, specialized UV coatings having wavelength-converting properties are commercially available from Eureca Messtechnik GmbH, Germany. However, other types of wavelength-converting materials may be employed, such as fluorescent inorganic or organic materials.

Figure 6:
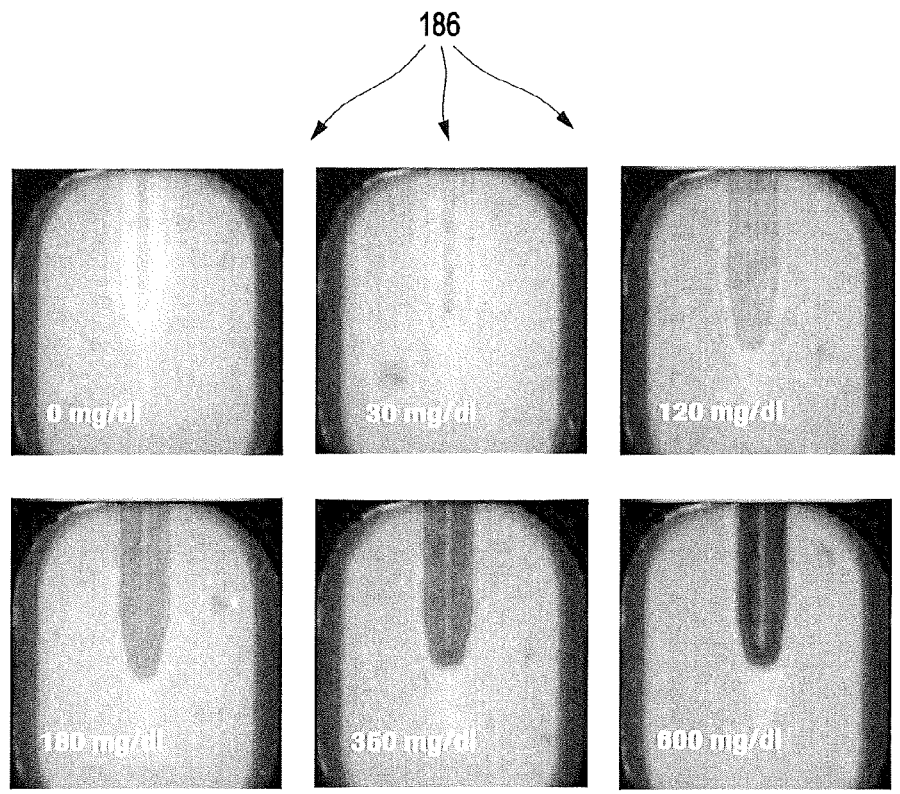
FIG. 6 shows a series of images acquired with samples of blood containing different concentrations of glucose.

After wetting of the test field 162 by the sample of the body fluid, i.e. after application of the sample of the body fluid to the test field 162, the above-mentioned detection-reaction will take place, leading to optically detectable changes in the test field 162 and/or the test chemistry 154 contained therein. Examples of different images of the test field 162 as acquired by an image detector 178 are depicted in FIG. 6. Therein, the different images denote different types of samples of body fluid, in this case blood, containing different concentrations of the analyte to be detected, in this case glucose. The concentrations of the analyte are given in the images, denoted in milligrams per deciliter (mg/dl). As can be seen, from the gray values of the images 186 or the changes of these gray values, a concentration of the analyte may directly or indirectly be derived. Thus, the color changes and/or the changes of the gray values in the images 186 may be registered and observed until a specific end point at which the detection reaction has been completed. For this purpose, changes or change rates of the images 186 may be observed and compared to one or more thresholds, wherein, in case a change over a predetermined time is below a given threshold, an end point of the detection reaction may be detected and the image at this end point may be evaluated for determining the analyte concentration. Examples of processes for deriving the analyte concentration from the images 186 and/or for an end point determination of the detection reaction are provided in the above-mentioned EP 0 821 234 A2 as well as in EP 0 974 303 A1.

Thus, by evaluating the images 186, the concentration of the analyte may be determined, by directly or indirectly evaluating the information provided in a time-sequence of the images 186, which, herein, is referred to as an image sequence 186. Preferably, the image detector 178 may comprise a grid of photosensitive elements 180 having a dimension of 20 µm to 50 µm, preferably 30 µm, in each direction. However, other dimensions are possible. Further, several photosensitive elements 180 of the image detector 178 may be combined to form combined photosensitive elements 180, wherein the information provided by these combined photosensitive elements 180 is combined and regarded as information of a superpixel of the image detector 178. In the present specification, this option shall be included, independent from the fact whether the raw photosensitive elements 180 of the image detector 178 are used or if several photosensitive elements 180 are combined, thereby creating an image detector comprising an array of superpixels.

Figure 7:
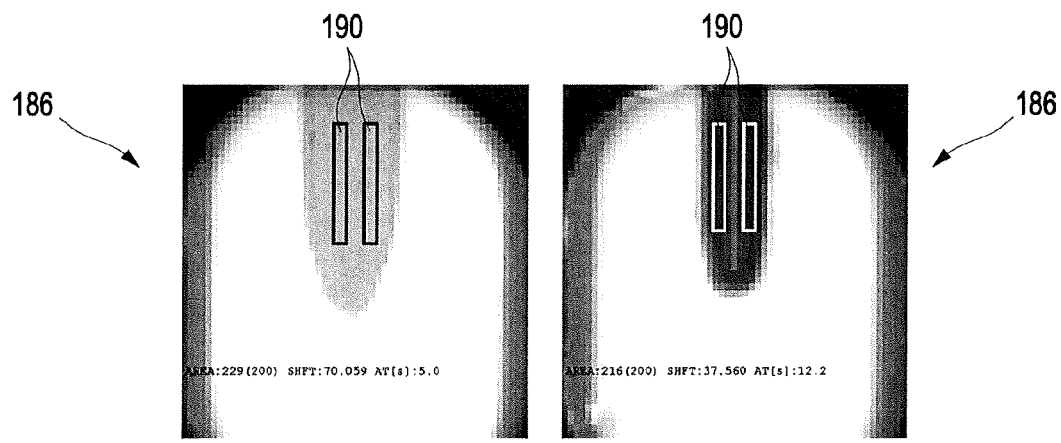
FIGS. 7 and 8 show different options of detecting a region of interest.
Figure 8:
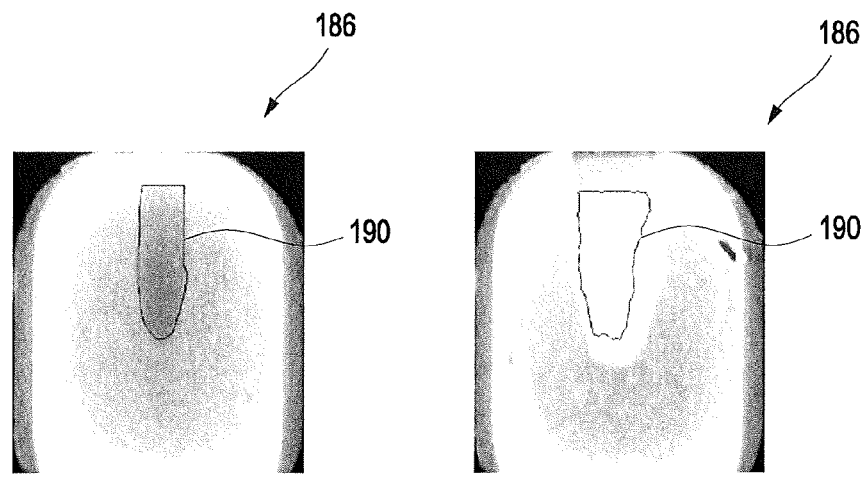

Typically, which is also possible within the present invention, only a portion of the images 186 is evaluated for determining the analyte concentration. Thus, a region of interest has to be defined, which defines the pixels of the image 186 which are considered for determining the analyte. In FIGS. 7 and 8, several options for determining the region of interest (denoted by referential 190) are depicted. Thus, as depicted in FIG. 7, fixed areas of the images 186, such as pre-determined rectangular areas, may be used as regions of interest 190. This is due to the fact that, typically, the application of the sample by the sample transfer disclosed in FIG. 5C takes place more or less at a pre-determined position, leading to regions of sample transfer corresponding to the one or more capillary channels 148, as can be seen in the images 186 depicted in FIG. 7.

Therein, the images 186 in this figure are generated by using samples having different analyte concentrations.

The option depicted in FIG. 7 using pre-determined regions of interest 190, however, requires very tight position tolerances, specifically tight tolerances with regard to sample transfer and/or tolerances with regard to the geometry of the micro-samplers 142, the detector 176 and the overall test elements 124.

Therefore, as will be outlined in further detail below, a second option for determining the region of interest 190 is an analysis of the image sequence of the images 186 in an early phase of the wetting of the test field 162 with the sample of the body fluid and/or in an early phase of the process of the detection reaction. In this option, changes in the information contained in the pixels of the images 186 may be evaluated, which are caused by the wetting of the test field 162 after the transfer of the sample fluid. Specifically in case a signal-to-noise-ratio of the images 186 is sufficient, only wetted areas may be evaluated after the end point is reached, which may lead to a significant reduction of data storage volume and evaluation time.

As a third option, which may be combined with the second option listed above, changes in the information values stored in the pixels of the images 186 of the image sequence may be evaluated for determining the region of interest. Thus, for detecting changes in the images 186, at least two of the images 186 may be compared, and the region of interest 190 may be determined on the basis of these detected changes. Thus, pixels of the images 186 may be selected based upon their history, such as by assigning those pixels with the highest rate of change in a certain time span to the region of interest 190. In FIG. 8, two images 186 of the image sequence are depicted at different times, wherein the right image is acquired at a later point in time as compared to the left image. Different images 186 obtained from variations in capillary geometry, transfer step and reagent film compositions may be used, and, by choosing an appropriate method for determining the region of interest 190, artifacts, color inhomogeneity, trapped air bubbles and time-dependent changes of the signal may be compensated.

As outlined above, the method according to the present invention comprises at least one correcting step correcting a relative position change between the image detector 178 and the test field 162 in the image sequence. As outlined above, the term relative position change may refer to any type of movement of the test field 162 as seen by the detector 176 and, specifically, by the image detector 178. This type of movement may be due to internal and/or external reasons in the test system 110. Thus, movements and corresponding position changes may be due to a handling of the test system 110, e.g. to mechanical vibrations during handling of the device 112 by a user, since, preferably, device 112 may be a hand-held device. Additionally or alternatively, movements may be due to the action of the test system 110 itself, i.e. to internal reasons. Thus, the application of the sample of the body fluid onto the test field 162, as depicted in FIG. 5C, may lead to a movement and/or a distortion of the test field 162 itself, since, preferably, the micro-sampler 142 may get in direct contact with the test field 162 or may even be pressed onto the test field 162, thereby exerting mechanical forces. Thus, as used in the present invention, any type of movement of the test field 162 or parts thereof and/or any type of distortion of the test field 162 or parts thereof, as seen in the image detected by the image detector 178, may be comprised in the term relative position change.

According to the present invention, this relative position change between the image detector 178 and the test field 162 in the image sequence comprising images 186 acquired at different times is, at least partially, corrected. An example of a correction process will be explained with reference to FIGS. 9 and 10A, 10B in the following.

Figure 9:
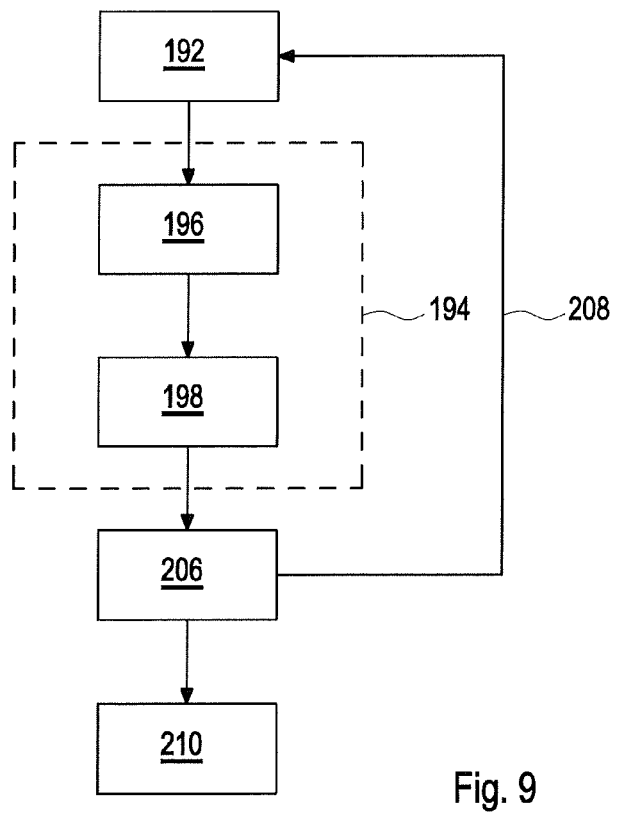
FIG. 9 shows a block diagram of an example of a correction of a relative position change in an image sequence.

Thus, FIG. 9 shows a schematic block diagram of a method according to the present invention, leading to a corrected image sequence. In a first step, step 192, a new image 186 is acquired. This new image 186, belonging to an image sequence of uncorrected images, is corrected in at least one correction step 194. Therefore, at least one characteristic feature of the test field 162 is detected in the image (step 196) and the correction step 194 is performed on the basis of the characteristic feature. The actual correction of the image 186 is denoted by process step 198 in FIG. 9.

Figure 10:
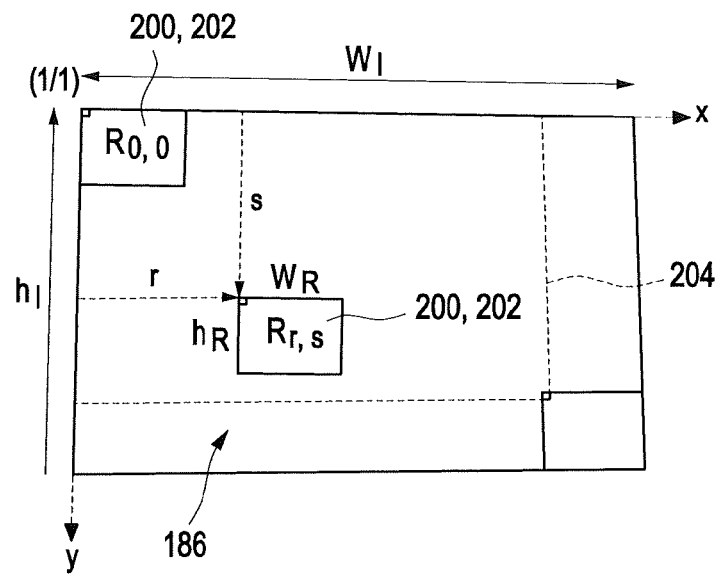
FIGS. 10A and 10B show an example of an image comparison for the purpose of position correction.
Figure 10:
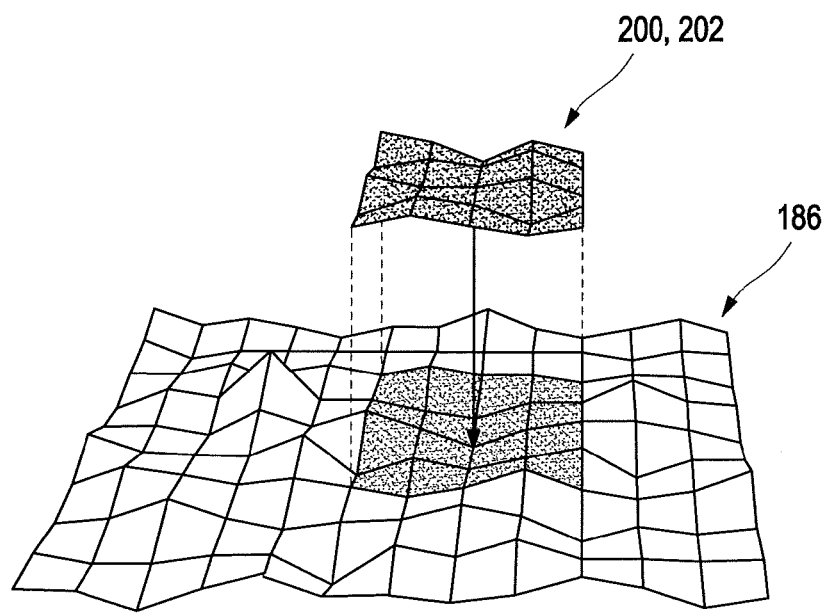

As an example for a correction 198 based on the detection 196 of at least one characteristic feature, reference may be made to FIGS. 10A and 10B. Thus, the image 186 to be corrected, i.e. the image as acquired in acquisition step 192, may be compared with one or more reference images. Thus, as an example, the first image of an image sequence may be used as a reference image, and all images of the image sequence subsequently acquired may be corrected to be in positional conformity with this reference image. However, basically any other image of the image sequence may be used as a reference image, even combinations of several images.

Thus, in FIG. 10A, a portion 200 of the image 186 to be corrected may be chosen as a characteristic feature 202, including the information values as stored in this portion 200. Therein, from the point of view of the present invention, the portion 200 both may be a portion of the reference image, and corresponding portions in the image to be corrected may be searched, and/or the portion 200 may be a portion of the image to be corrected, and corresponding portions in the reference image may be searched. Both options are possible and shall be comprised in the method according to the present invention. In the following, the option of defining the characteristic feature 202 in the reference image will be explained as an example, without restricting the scope of the invention.

Each image 186, including the reference image, may be described as a matrix comprising a number of information values I in each position or pixel of the image 186, such as follows:

$$I = \begin{bmatrix} I_{1,1} & \cdots & I_{1,N} \\ \vdots & \ddots & \vdots \\ I_{M,1} & \cdots & I_{M,N} \end{bmatrix}.$$

Therein, $I_{i,j}$ denote the information values of the pixel i, j of the image I, such as gray values. N and M are integers denoting the width of the image 186 (N) and the height of the image (M). One specific position of this matrix, denoted by the coordinates i, j with $1 \leq i \leq M$ and $1 \leq j \leq N$, denotes a specific pixel or position of the image 186.

As indicated in FIG. 10A, a characteristic feature 202, being a portion of a reference image, is selected, and a search for this characteristic feature 202 in the image 186 to be corrected is performed. For this purpose, the portion 202 of the reference image, again, is shifted over the matrix I of the image 186 to be corrected. The portion 200 itself may be represented by a matrix having smaller dimensions than the matrix I. The portion 200 is shifted by r in an x-direction and by s in a y-direction, over a search region 204, which is smaller than the image 186 to be searched, itself. Starting with r=0 and s=0, the maximum values to be assumed by r and s during the shifting process are: $r_{max}=M-h_R$, with $h_R$ being the height of the portion 200, and $s_{max}=N-w_R$, with $w_R$ being the width of the portion 200. In FIG. 10A, $w_I$ denotes the width of the image 186, and $h_I$ denotes the height of the image 186.

For every possible value of the shift (r,s), a degree of conformity and/or a degree of identity or similarity is determined for the portion 200 and the corresponding portion of the image 186 to be searched. This is schematically depicted in FIG. 10B. Thus, with R denoting the characteristic feature 202 or portion 200 to be searched in the image 186, a search for shift coordinates (r,s) is performed for which the corresponding portion 200, 202 of the image I corresponds to the portion R. As an example, for each value pair (r,s), the following sum of squared differences may be determined:

$$d_E(r,s) = [\Sigma_{(i,j)\in R}(1(r+i,s+j)-R(i,j)^2)]^{1/2}.$$

By shifting the characteristic feature 202 (i.e. by shifting R) over the whole image 186 to be searched, one $d_E$ may be determined for each shift (r,s). Finally, by comparing all $d_E(r,s)$ determined this way, a minimum of all $d_E$ may be determined, i.e. a specific shift (r,s) may be determined for which $d_E$ assumes a minimum value. This shift denotes a best guess of a search result of the search for the characteristic feature 202 in the image 186. In order to avoid artifacts, this candidate of a shift may be compared to one or more limit values, i.e. by comparing the minimum value $d_{E,min}$ with at least one limit value. Only if $d_{E,min}$ is smaller or almost as big as the limit value, a positive match may be detected.

It has to be noted, however, that the above-mentioned sum of squared differences is only one algorithm out of a large number of possible algorithms suited for searching for pattern matches for finding characteristic features in the image 186. This algorithm of finding pattern matches is e.g. disclosed in W. Burger et al.: Image Processing, Springer Verlag, London, 2008, pp. 429-436. However, additionally or alternatively, other types of pattern match algorithms searching for characteristic features in images 186 may be used, in order to determine a shift in between images.

As soon as the search for the characteristic feature 202 in the image 186 was successful, the search will return a shift (r*,s*), indicating the amount of relative position change in between the image 186 and the reference image. This shift (r*,s*) may be used in method step 198 in FIG. 9 for performing the correction of the image 198, thereby creating a corrected image (step 206 in FIG. 9) and at this corrected image to a corrected sequence, containing the sequence of corrected images. For this purpose, the following correction of the matrix I of the image 186 may be performed:

$$I^*(i,j)=I(i+r^*,j+s^*), \text{ with } 0 \leq i < M \text{ and } 0 \leq j < N.$$

For r*=0 and s*=0: I*=I.

As an example, r* and s* may be limited to plausible values, such as values not exceeding 50. Instead of adding the shift (r*,s*), as indicated above, a subtraction is also possible.

For further details of the potential algorithm for the correction step 194 and/or for further optional embodiments, reference may be made to the above-mentioned publication W. Burger et al.: Digital Image Processing, Springer Verlag, London, 2008, pp. 429-436. Specifically, the template matching algorithm disclosed in this text passage may be applied to the correction algorithm or the correction step 194. It should however be noted that other types of correlation and/or matching algorithms may be used, such as cross-correlation algorithms and/or pattern recognition algorithms. Further, it should be noted that the algorithm disclosed as an exemplary embodiment above, with regard to the examples provided in FIGS. 10A and 10B, merely refers to position changes which may be described by a shift in an x-direction and/or a shift in a y-direction. However, a large number of other correction algorithms may be used. Thus, with a similar algorithm as disclosed above, rotational changes may be detected, such as by using a rotation parameter instead of the translational parameters (r,s) and searching for pattern matches. Further, by using similar algorithms, a distortion of the images 186 may be detected and corrected for in step 198 in FIG. 9.

The whole correction step 194 in FIG. 9 may be performed repeatedly, such as once for every newly acquired image (step 192). In FIG. 9, this is indicated by repetition 208. The repetition 208 may be performed for each newly acquired image, as indicated in FIG. 9, as an on-line correction process. However, other time sequences for correction may be applied, such as applying the correction step 194 to the whole sequence of images and/or to a plurality of images 198, i.e. by simultaneously correcting a plurality of images 186.

Further, as indicated by reference number 210 in FIG. 9, the sequence of corrected images or corrected sequence may then be used for further evaluation. Thus, all further steps for evaluating 210 images 186 of the image sequence for the purpose of detecting the at least one analyte in the sample of the body fluid may be based on the corrected images and/or the corrected image sequence. Thereby, as outlined in detail above, the precision of all further steps may be greatly improved.

Figure 11:
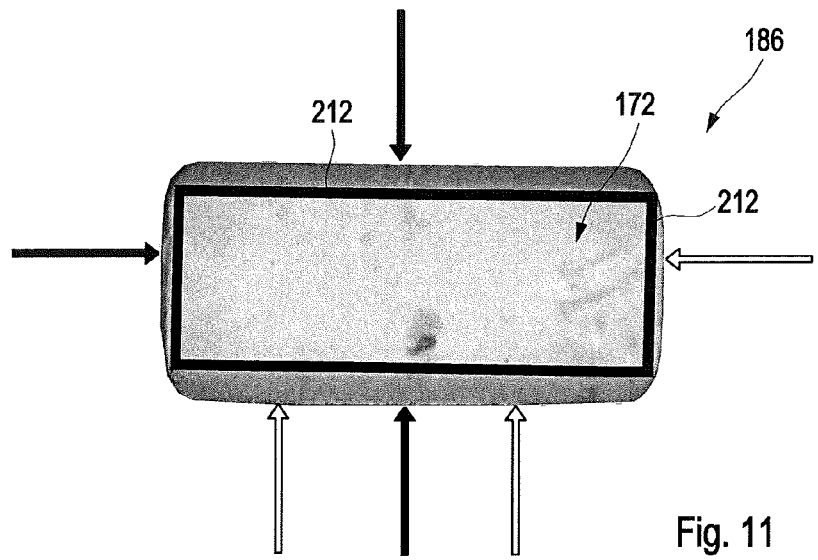
FIG. 11 shows an example of a detection of a test field and/or a viewing window.

The images 186 which are subject to the correction algorithm, such as the correction algorithm of FIG. 9, not necessarily have to contain the whole image information as rendered by the image detector 178. Thus, as may be seen in the exemplary images 186 in FIGS. 6-8, part of this image information rendered by the image detector 178 may be outside the actual visible window or viewing window 170, as depicted in FIG. 5B. Thus, before or after evaluation of the images 186, boundaries of the test field 162 and/or boundaries of the visible window of the test field 162 may be detected, either in the raw images to be corrected in the correction step 194 or in the corrected images of the corrected image sequence. This step, preferably, is performed in the corrected image sequence, since, in this case, the test field 162 and/or the boundaries of a visible window of the test field 162 may be provided in an absolute coordinate system of the corrected images, i.e. may be valid for all corrected images of the corrected image sequence. Thus, as depicted in FIG. 11, the viewing window 170 and/or visible window (both terms are used as synonyms herein) may be detected by evaluating the information values in the image matrices. Thus, e.g. by using a gray-scale edge detection of the images rendered by the image detector 178, before or after correction, boundaries 212 may be detected, such as boundaries in x-direction and/or boundaries in y-direction. When using an edge detection for detecting the boundaries 212, the edge detection algorithm of choice may be an algorithm tolerant against debris or similar image disturbances. For subsequent analysis, the images 186 may be reduced to the area within these boundaries 212, in order to reduce the data amount. Further, additionally or alternatively, a position and/or rotation of the viewing window 170 may be detected in the images 186 and/or in the corrected images. Thus, the term image, as outlined above, not necessarily has to refer to the whole amount of information provided by the image detector 178. A data reduction may take place in one or more steps of the method according to the present invention, such as by reducing the images 186 to reduced images or corrected reduced images, which only contain information values inside the test field 162 and/or inside the viewing window 170 or visible window of the test field 162. Both options are referred to when using the term image 186.

Further, in conventional methods for qualitatively and/or quantitatively detecting an analyte concentration, the determination of a blank value and/or an empty value (both terms will be used as synonyms herein) typically plays an important role. Thus, since the optical properties of different patches of test fields 162 or test chemistries 154 may differ even in a dry state, the blank value may be used for normalizing detected optical changes which actually are due to the detection reaction. Typically, in known methods, such as in WO 2012/010454 A1, one or more blank values are acquired before applying the sample of the body fluid to the test field 162 and, after sample application, the subsequent measurement values are normalized by using this blank value, such as by dividing all subsequent measurement values rendered by the detector 176 by the at least one blank value.

The present invention, specifically the correction step 194, offers the possibility of generating, at a very high precision, an averaged blank image rather than a single blank value, the averaged blank image containing averaged information of a plurality of blank images.

Figure 12:
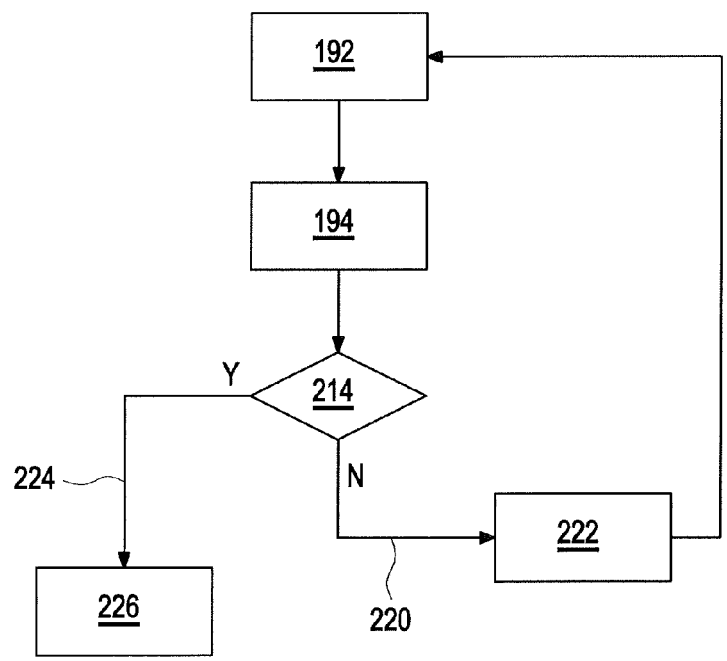
FIG. 12 shows an algorithm for determining an averaged blank image.

In FIG. 12, an embodiment of an algorithm for generating an averaged blank image is disclosed in a schematic block diagram. The averaged blank image may also be referred to as an averaged dry empty picture. The algorithm as depicted in FIG. 9 may be implemented into the method according to the present invention.

In a first step, a new image 186 is acquired by using the image detector 178, as denoted by method step 192 in FIG. 12. As explained with regard to FIG. 11 above, this newly acquired image may be reduced to an actual image within the boundaries 212 of the viewing window 170. Further, one or more correction steps 194 may be performed, such as by using the algorithm as explained with regard to FIG. 9 above. The optional detection of the viewing window 170 may be performed by using the uncorrected, raw images and/or by using the corrected images.

Subsequently, in the newly acquired image or in the newly acquired, corrected image, at least one step 214 of detection of sample application is performed. This detection of sample application provides an answer to the question whether, in between the acquisition of the preceding image and the present, newly acquired image, the sample of the body fluid was applied to the test field 162. This step 214 of detection of sample application may be performed by detecting changes in the information values I(i,j) of the image or corrected image, as compared to the preceding image. As an example, changes of averages of the information values contained in the images or corrected images may be calculated and used, such as by using the following formula:

$$|\overline{\Delta I_n}| = \left| \frac{\Sigma_{i,j} I_n(i, j)}{M \cdot N} - \frac{\Sigma_{i,j} I_{n-1}(i, j)}{M \cdot N} \right| = \frac{1}{M \cdot N} (\Sigma_{i,j} I_n(i, j) - \Sigma_{i,j} I_{n-1}(i, j)),$$

wherein $|\overline{\Delta I_n}|$ denotes a difference averaged value of the neighbouring images $I_{n-1}$ and $I_n$, wherein $I_n(i,j)$ denotes the information value of the pixel (i,j) of the newly acquired image or the corrected newly acquired image, and wherein $I_{n-1}(i,j)$ denotes the corresponding information value of the pixel (i,j) of the previously acquired image or the previously acquired corrected image.

The difference averaged value $|\overline{\Delta I_n}|$ may optionally further be standardized to the average information contained in image $I_n$, in order to obtain a relative differenced averaged value:

$$|\Delta I_{n,rel}| = \frac{|\overline{\Delta I_n}|}{\frac{\Sigma_{i,j} I_n(i, j)}{M \cdot N}}$$

Figure 14:
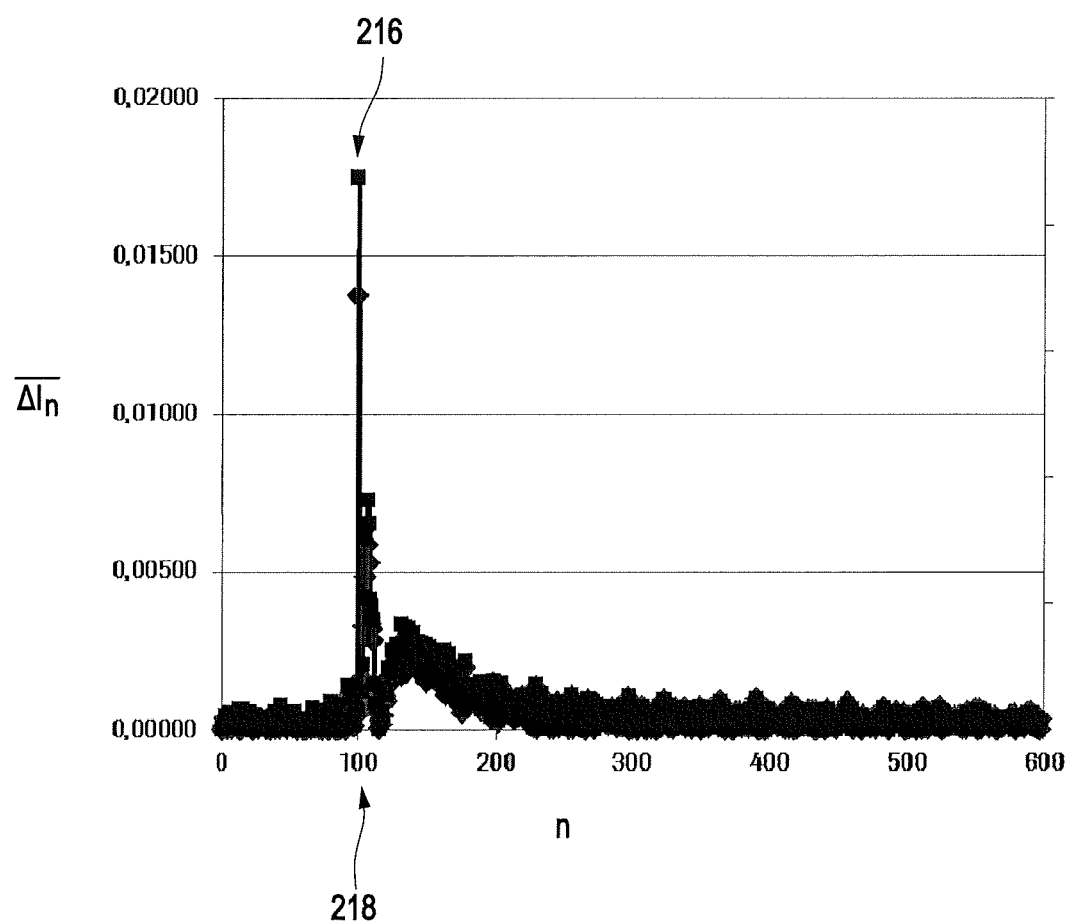
FIG. 14 shows an example of detection of the moment of sample transfer onto a test field.

In the following, $|\overline{\Delta I_{n,rel}}|$ also so referred to as $\overline{\Delta I_n}$. In FIG. 14, $\overline{\Delta I_n}$ is depicted as a function of the image number n. Therein, the whole images may be evaluated, or only part of the images 186. Thus, only the part of the images within the boundaries 212 of the viewing window 170 may be evaluated. The graph shows a significant peak 216. The image number n or, which is equivalent as an indicator of a time variable, the number or identifier of the image in which the peak 216 is detected denotes the moment 218 of sample application. Thus, by generating appropriate values indicating the changes of the information contained in the images 186, preferably the corrected images, the moment 218 of sample application may easily be detected. Further, optionally, an image 186 of the image sequence which was or is acquired closest to the moment 218 of sample application may be determined, this image being referred to as a touchdown image.

Returning to the algorithm for detecting the averaged blank image in FIG. 12, for each newly acquired image or newly acquired corrected image, an appropriate test may be performed indicating if a sample application has taken place or not. This detection 214 of sample application, for example, may use the algorithm as disclosed above, or, additionally or alternatively, any other type of algorithm detecting significant changes due to the sample application.

In case no sample application has been detected (branch N in FIG. 12, denoted by reference number 220), the newly acquired image, preferably the newly acquired corrected image after performing the correction step 194, may be added to a preliminary averaged blank image (step 222 in FIG. 12), on a pixel-by-pixel basis. For this purpose, the following formula may be used:

$$B_{pr,n}(i, j) = \frac{1}{n} \cdot [(n-1) \cdot B_{pr,n-1}(i, j) + I_n(i, j)],$$

wherein $B_{pr,n}$ denotes the $n^{th}$ averaged blank image (pixel i,j), and $I_n$ denotes the newly acquired $n^{th}$ image mage before sample application (pixel i,j). As an initial value for $B_{pr,1}$, the first blank image $I_f$ may be used. Thus, an averaged blank image $B_{pr,n}$ may be generated by using a moving algorithm, by updating the preliminary averaged blank image $B_{pr,n}$. Finally, as soon as the sample application has been detected (branch Y in FIG. 12, denoted by reference number 224), the most recent averaged blank image may be used as the final blank image, thereby defining the averaged blank image B (step 226 in FIG. 12), by using the following formula:

$$B(i,j) = B_{pr,n}(i,j).$$

This averaged blank image B may be used as a reference for all subsequent changes of the images which are due to the sample application.

Thus, the averaged blank image B may be used for determining the analyte concentration by normalizing the images or corrected images, preferably after sample application, to the averaged blank image B on a pixel-by-pixel basis, such as by transforming the images (i.e. one image, a plurality of images or even all images) in one or both of the following transformed matrices:

$$I'(i,j) = I(i,j)/B(i,j)$$

or $$I''(i,j) = I(i,j) - B(i,j)$$

or $$I'''(i,j) = (I(i,j) - B(i,j))/B(i,j).$$

Additionally or alternatively, as outlined above, at least one touchdown image T or corrected touchdown image may be used for determining the analyte concentration. Thus, as an example, one or more of the following transformed matrices may be used for determining the analyte concentration:

$$I''''(i, j) = I(i, j) - T(i, j)$$

or $$I'''''(i, j) = \frac{I(i, j) - T(i, j)}{B(i, j)}$$

The latter formula corresponds to the comparison matrix $C_n$ as defined above, which may also be used for detecting significant changes for the purpose of detecting a region of interest in the image sequence and/or the corrected image sequence.

Other types of normalization processes are possible. In the following, when reference is made to the evaluation of the image sequence or corrected image sequence for the purpose of determining the analyte concentration, both the possibility of using the images or corrected images or the possibility of the normalized, transformed images or corrected images, such as by using one or more of the preceding formulae, shall be possible.

Further, as outlined above, the determination of a region of interest plays an important role in many processes for detecting analytes in a body fluid. The method according to the present invention, specifically by creating the corrected image sequence, such as by using the algorithm depicted in FIG. 9, allows for a highly precise determination of the region of interest 190, specifically and preferably on a pixel-by-pixel basis in the corrected images.

Figure 13:
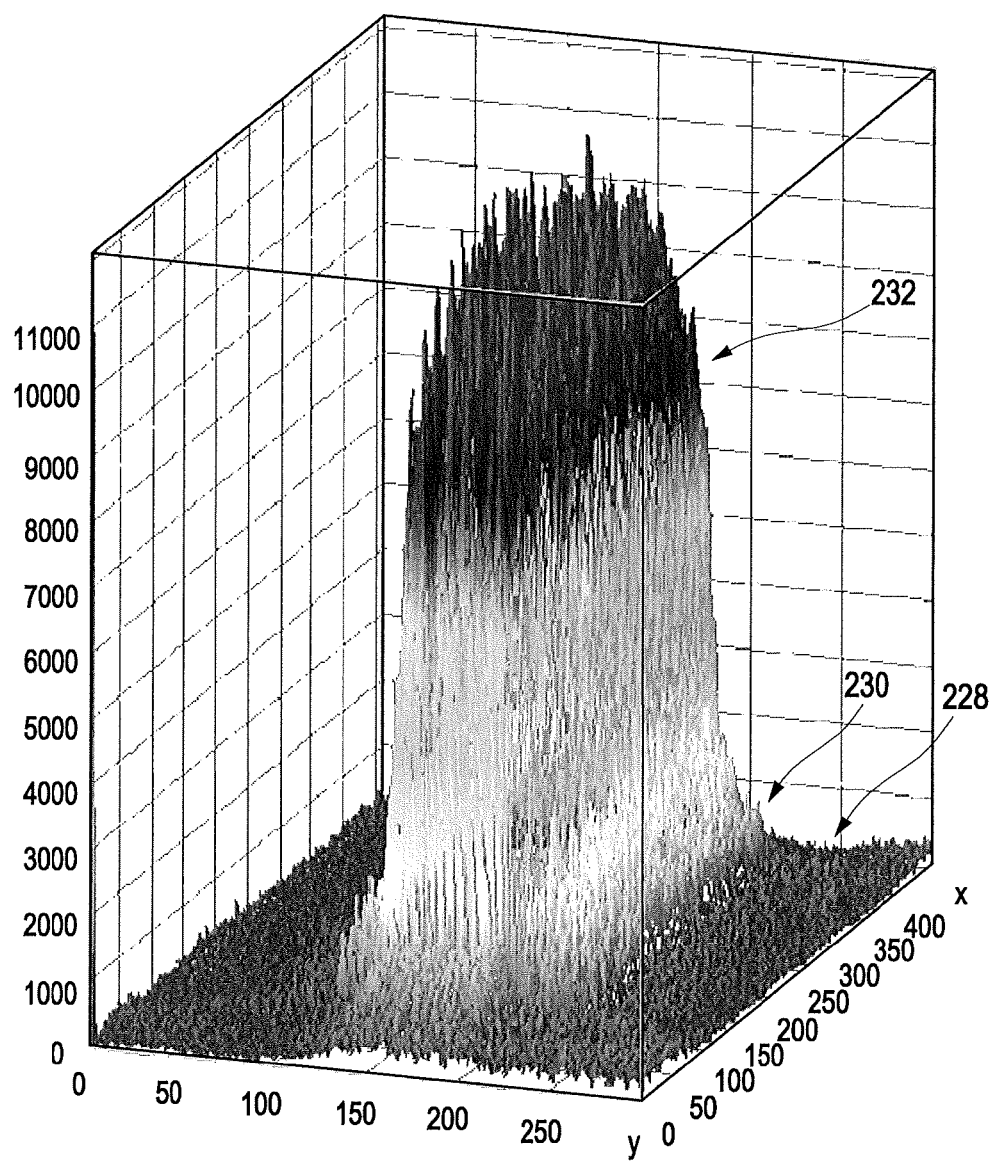
FIGS. 13A and 13B show an example of detecting significant changes in an image sequence by using histograms.
Figure 13:
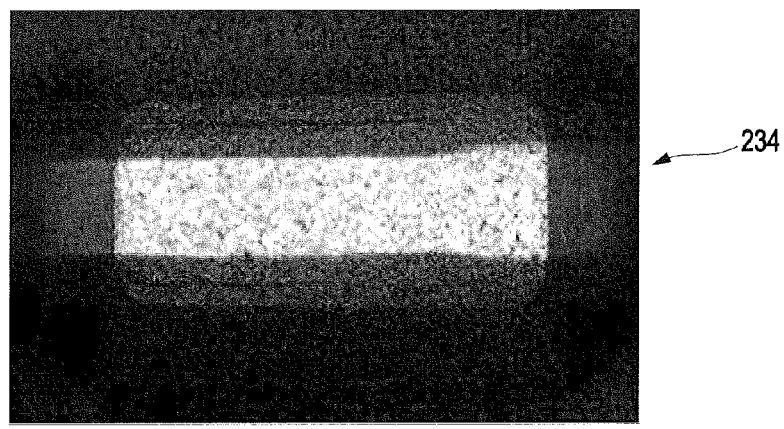
Figure 13:
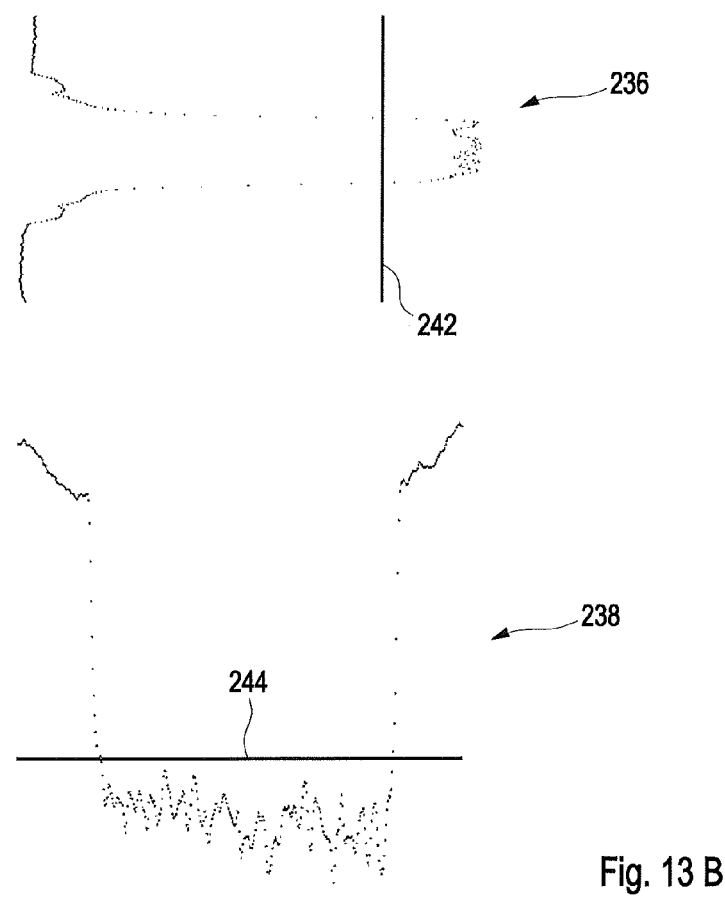

Firstly, as depicted in FIGS. 13A and 13B, a detection of significant changes may take place in order to define the region of interest 190 and/or a preliminary region of interest. For this purpose, changes in the information values contained in the images or, preferably, the corrected images, are evaluated. As an example, the following so-called difference matrix denoting the changes of the information values of the images may be used:

$$dI(i,j)=I_m(i,j)-I_n(i,j),$$

wherein dI denotes a matrix indicating the change in information values and wherein $I_m$ denotes an image or corrected image or combined or transformed image acquired after the moment 218 of sample application and wherein $I_n$ denotes an image, a corrected image or a transformed or combined image acquired before or during the moment 218 of sample application. As an example, $I_n$ may be the above-mentioned touchdown image T. However, other embodiments are feasible, such as embodiments in which $I_n$ is an image acquired before the moment of sample application. Preferably, the images $I_m$ and $I_n$ are acquired as close as possible to the moment 218 of sample application. Thus, $I_n$ may be the image acquired immediately before the moment of sample application, and $I_m$ may be the image acquired immediately after sample application. Additionally or alternatively, images acquired at predetermined time distances before and after sample application may be compared, such as by using the image acquired one second before sample application as image $I_n$ and the image acquired one second after sample application as the image $I_m$. Alternatively, $I_n$ may be the touchdown image, and $I_m$ may be an image acquired at a point in time 0.5 s to 4 s after the moment of sample application, such as 1 s after the moment of sample application. Further, several images may be combined, such as by using a preliminary averaged blank image instead of image $I_n$ and/or by using the averaged blank image B instead of image $I_n$.

In FIG. 13A, an example of the information values contained in the matrix dI is drawn in a three-dimensional plot. Therein, x and y denote the pixel coordinates, and z denotes the information value of the corresponding pixels (i,j) of the matrix dI, such as a gray value. In the exemplary embodiment of FIG. 13A, significant changes may be detected. In case no significant relative changes are detected in the matrix dI, several images may be combined, such as more than one image acquired after sample application, in order to detect significant changes.

As can be seen in FIG. 13A, significant changes are typically found all over the area of the test field 162, partly in form of spikes, due to chemical inhomogeneities. The plot in FIG. 13A further shows distinct regions. Therein, a background region 228 may be detected, a region of unwetted test field 230 and an actual region of significant changes 232 which, later on, may be a candidate for the region of interest 190.

In order to define the region of interest 190 or a rough estimation of the region of interest 190, a threshold method may be used, for example by using an algorithm as depicted in FIG. 13B. In this algorithm, the image of changes, as denoted by the matrix dI above, is denoted by the reference number 234. The image of changes 234 was acquired with a blood sample having a concentration of glucose of 556 mg/dl. In this image of changes 234, average values of lines (plot 236 in FIG. 13B) and average values of columns (reference number 238) may be formed by averaging the information values of the matrix dI over each line and each column, respectively. These averaged values may be compared to one or more thresholds, denoted by reference numbers 242 and 244 in FIG. 13B. By averaging over the lines and/or columns, spikes in the matrix dI may be removed. Further, a filtering of averaged values may be applied. By using the threshold method as depicted in FIG. 13B and/or by using other types of threshold methods, plateaus in the matrix dI, indicating a region of significant changes, may be detected, and coordinates of borderlines of this region of interest 190 and/or a rough estimation of the region of interest may be generated. Thus, the outermost columns at which the plot 236 crosses threshold 242 may be used as column coordinates for the region of interest, and the outermost coordinates at which plot 238 crosses threshold 244 may be used as line coordinates for the region of interest, thereby generating a rectangular region of interest 190. In addition to simply crossing the threshold, other criteria may be used. Thus, an additional criterion may be that a predetermined number of subsequent values of the plots 236, 238 also exceed the threshold values 242 or 244, respectively.

Additionally or alternatively to the rough estimation of the region of interest by using the averaging threshold method depicted in FIGS. 13A and 13B, more pixel-oriented methods may be used, as will be explained in more detail with respect to FIGS. 15 and 16.

Figure 15:
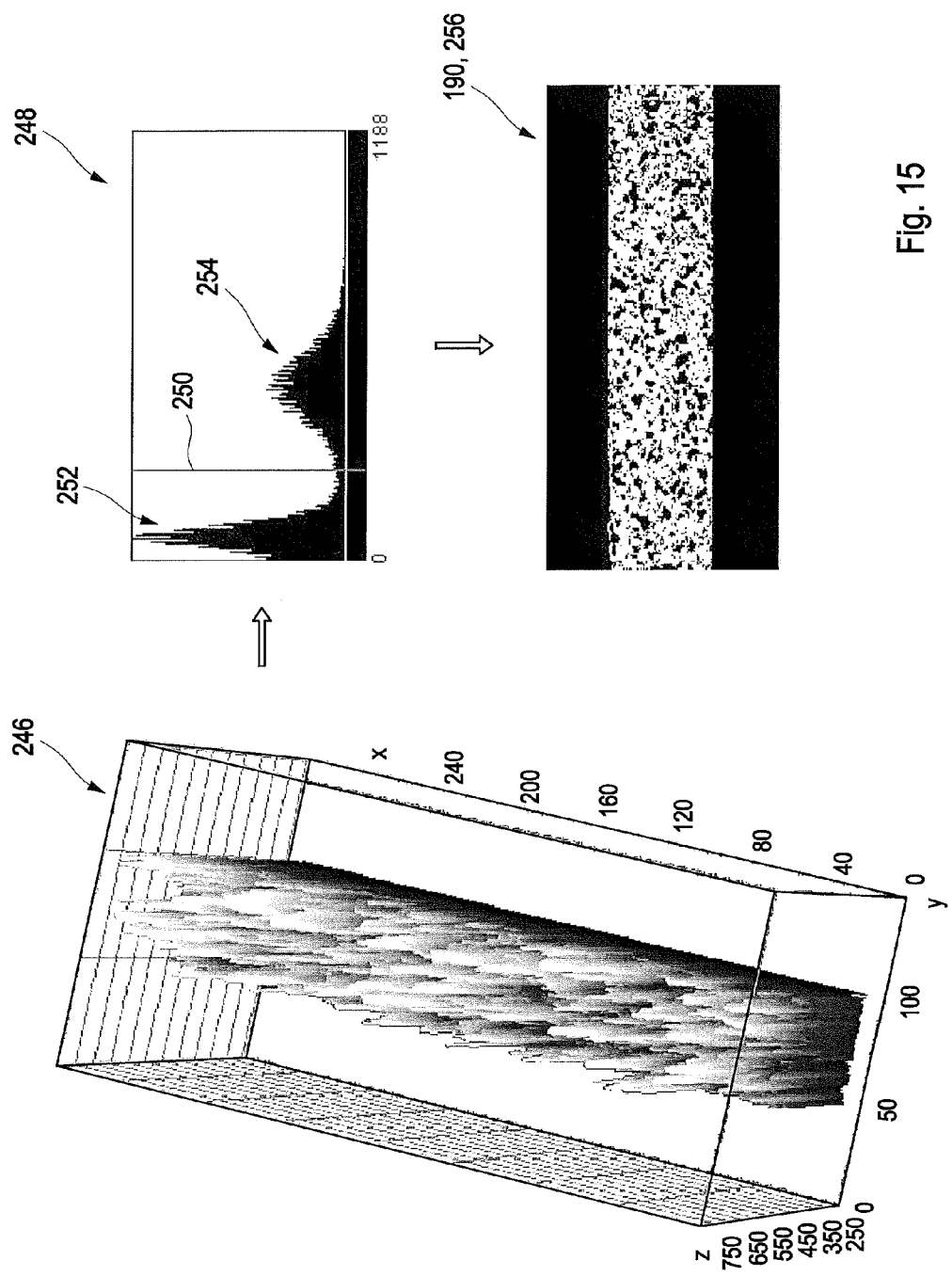
FIGS. 15 and 16 show an example of defining a region of interest on a pixel-by-pixel basis.

Thus, the method depicted in FIG. 15 may start with the preliminary, rectangular region of interest 190, as determined by using the method in FIGS. 13A and 13B. Information values contained in the matrix dI outside the preliminary region of interest may be eliminated or replaced by 0. Additionally or alternatively, very small information values in the matrix dI may be cut off and/or replaced by 0. Further, other types of smoothing may be applied, such as a removal of spikes within average values. Thereby, an image of changes 246 may be generated as depicted on the left hand side in FIG. 15, in a similar plot as provided in FIG. 13A.

Further, a histogram method may be used for evaluating the image of changes 246, as indicated by histogram 248 in FIG. 15. In this histogram 248, the relative frequency for each gray value or information value contained in matrix dI (vertical axis) is plotted for each information value or gray value (horizontal axis).

Further, for evaluating the histogram 248, a further threshold method may be used. As outlined above, this threshold method may imply an automatic choice of one or more thresholds 250. For this purpose, threshold methods as known in the art may be used. Thus, preferably, the so-called Otsu method may be used. In this method, threshold 250 is chosen, separating the histogram 248 into two classes: class 252 of information values below threshold 250 and class 254 of information values above threshold 250, in the change matrix dI or a corrected change matrix dI, before or after filtering or applying additional data reduction steps. Threshold 250 may automatically be chosen such that the variance of values in each of the classes 252 is minimized, whereas the variance in between the values of different classes is maximized.

In a next step, all pixels belonging to class 252 may be eliminated from the region of interest 190. Thus, a region of interest 190 in the form of a binary mask 256 may be generated, as depicted in the right part of FIG. 15. Thus, the region of interest 190 may be defined by a binary matrix ROI with ROI(i,j)=1 in case pixel (i,j) is within the region of interest, and ROI(i,j)=0 in case pixel (i,j) is outside the region of interest 190. When plotting this binary mask 256, the black-and-white picture as depicted in FIG. 15 occurs.

Figure 16:
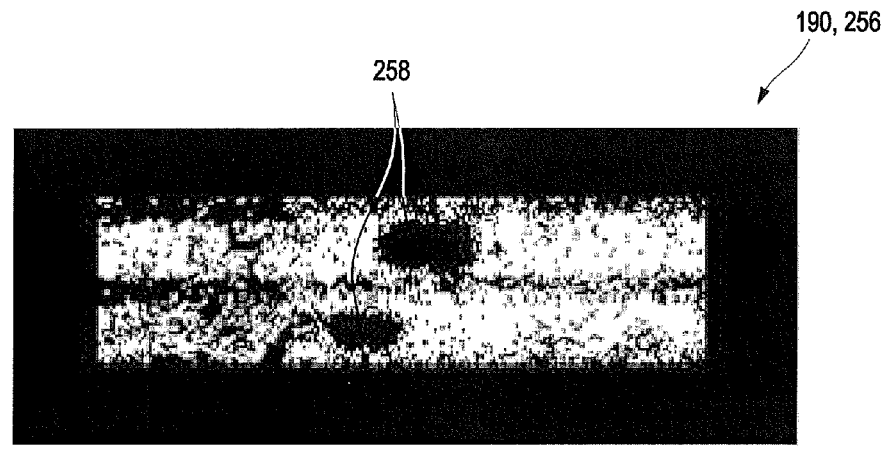

In FIG. 16, a more complex region of interest 190 denoted by a binary mask 256 is depicted, which typically may result when using micro-samplers 142 having two capillary channels 148, as depicted in FIG. 3A. In this case, the region of interest 190 and/or the binary mask 256 clearly shows two separate, horizontal white stripes, due to the parallel capillary channels 148. Further, the binary mask 256 may eliminate bubbles and/or debris, as denoted by black regions 258 in FIG. 16. Thus, this way of detecting the region of interest 190 on a pixel-by-pixel basis, by evaluating the images 186, preferably after the correction step 194, determines the region of interest 190 with a very high precision and confidence. Disturbances within the region of interest 190, such as disturbances caused by bubbles or debris, may reliably be removed by the thresholding process. The method may further be refined, such as by applying additional plausibility checks of the automatically detected region of interest 190, such as by performing plausibility checks regarding dimensions, number of relevant pixels or other types of plausibility checks of the region of interest 190.

The region of interest 190 defined on a pixel-by-pixel basis, by using the binary mask 256, may be used for evaluating the images 186, preferably after correction step 194, such as by evaluating the corrected images acquired after the moment 218 of sample application. Thus, the corrected images 186 after performing the correction step 194 may be transformed as follows:

$$I_{ROI}(i,j) = I(i,j) \cdot ROI(i,j).$$

Thereby, in any image, image sequence, group of images, corrected image or averaged image, all pixels outside the region of interest may be eliminated, whereas pixels inside the region of interest 190 may be kept unchanged. Thus, a masking of the images may take place.

For further evaluation and determination of the analyte concentration, the pixels of the images inside the region of interest, such as the pixels of the matrix $I_{ROI}$, may be evaluated. For this purpose, one or more of the images, corrected images or, for example, relative images such as one or more of the above mentioned images I', I'' or I''' may be masked, by using only the pixels of these images inside the region of interest. Thus, the above-mentioned image I''' may be used and masked for further evaluation, such as by using the following formula:

$$I'''_{ROI}(i,j) = I'''(i,j) \cdot ROI(i,j).$$

Thereby, a matrix indicating a change in remission or percent relative remission may be created. From this matrix $I'''_{ROI}$, average values over all pixels within the ROI may be created, wherein, basically, any type of averaging process may be used, such as median values over all pixels within the ROI, average values, weighted averages and other averaging processes.

Figure 17:
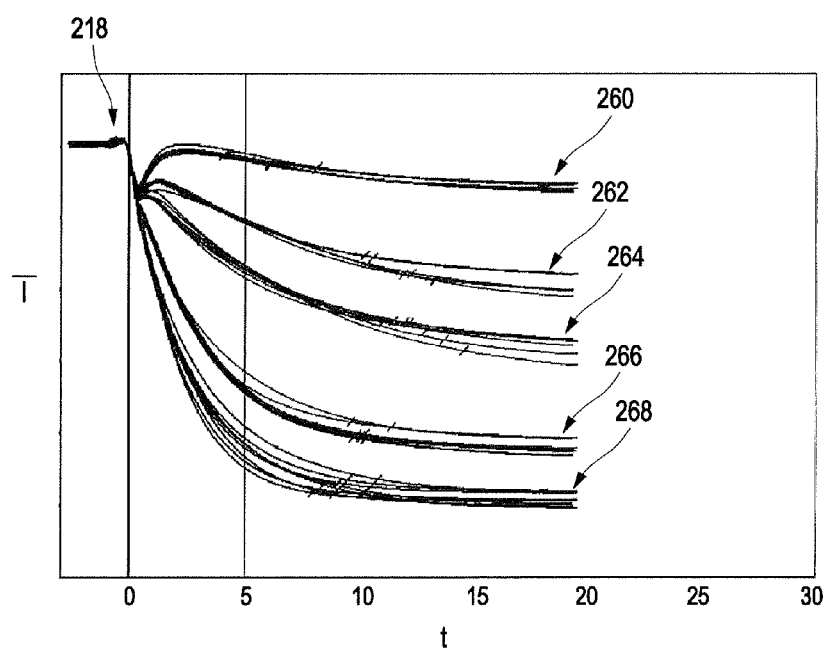
FIG. 17 shows an observation of a detection reaction for detecting blood glucose by observing averaged relative remissions over time for various glucose concentrations.

In FIG. 17, these average values $\bar{I}$ for several measurements are depicted (vertical axis), as a function of time t. Therein, the averaged values $\bar{I}$ are given in arbitrary units, such as by percent relative remission, and the time is given in seconds. The curves represent different concentrations of glucose in blood, wherein curve 260 denotes 20 mg/dl, curve 262 denotes 70 mg/dl, curve 264 denotes 150 mg/dl, curve 266 denotes 250 mg/dl, and curve 268 denotes 550 mg/dl. For each concentration, several plots are listed, indicating the low scattering of these curves 260 to 268. Further, in this plot, the moment 218 of sample application is marked by an arrow.

The curves 260 to 268 as depicted in FIG. 7 may further be evaluated, such as by using known methods for evaluation of reaction kinetics. Thus, for evaluating the concentration of the analyte, the value $\bar{I}$ may be determined at a predetermined time after sample application. Additionally or alternatively, as e.g. known from EP 0 821 234 A2 or EP 0 974 303 A1, an end point of the reaction may be determined by observing the changes in the curves 260 to 268. Thus, the change of the curves 260 to 268 may be observed over time and, in case the change over a predetermined time interval is below a predetermined threshold, an end point of the detection reaction may be determined. The value $\bar{I}$ at this end point may be used for calculating the analyte concentration, such as by using a defined algorithm transforming the end point value into a corresponding analyte concentration, as known in the art.

Figure 18:
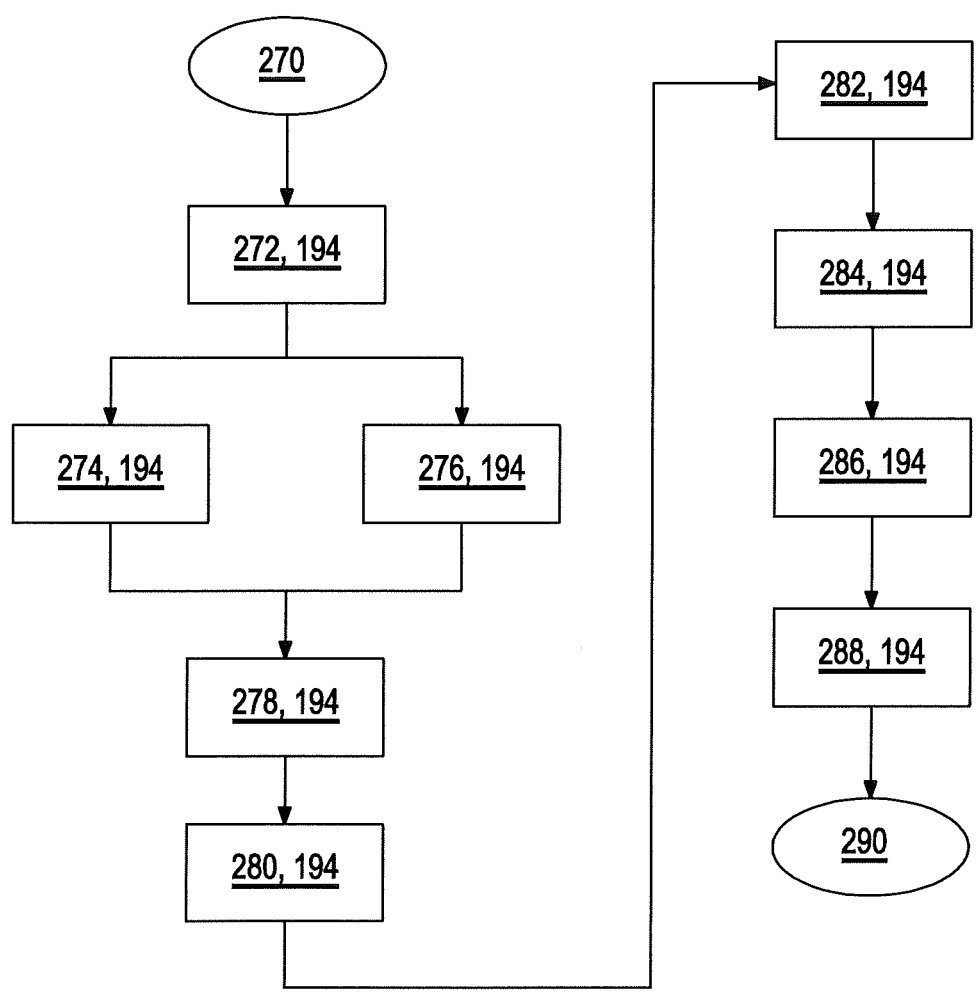
FIG. 18 shows a schematic block diagram of one potential embodiment of a method according to the present invention.

In FIG. 18, an overview of a potential embodiment of the method according to the present invention with several optional method steps is depicted as a block diagram. In a first optional method step after start 270, as disclosed with reference to FIG. 11 above, the test field 162 and/or the boundaries 212 of the viewing window 170 may be detected, preferably automatically (step 272). Further, in optional method step 274, as outlined above with reference to FIG. 14, the moment 218 of sample application, also referred to as the moment of touchdown, is detected. Further, preferably in parallel to the method step 274, the blank image and/or the averaged blank image may be detected, such as by using the process outlined above with reference to FIG. 12 (step 276).

Further, as outlined above with regard to FIGS. 13A, 13B, 15 and 16, significant changes due to sample application may be detected (step 278), significant changes may be processed (step 280), and the region of interest 190 may be determined (step 282).

Subsequently, in a series of further optional method steps, the reaction kinetics may be measured (step 284), the measurement results may be evaluated (step 286, analysis of measurement), and, further optionally, a statistical analysis of the measurement results may be performed (measurement statistics, step 288), before the method is ended (step 290).

When looking at the method depicted in FIG. 18, it turns out that no separate method step 194 (correction step) is depicted in this embodiment. This is due to the fact that the correction step 194 may be part of one, more than one or even all of the steps of the method according to FIG. 18. Thus, the detection of the test field in step 272 may be performed in conjunction with the correction step 194, i.e. by evaluating one or more corrected images. Further, the steps of detection of the moment of sample application (step 274) and the detection of the blank image or averaged blank image (step 276) may be performed in conjunction with the correction step 194, i.e. by using corrected images. Further, preferably, the significant changes in step 278 may be detected in conjunction with the correction step 194, i.e. by using one or more corrected images for detecting the significant changes. Similarly, as outlined above, the processing of significant changes (step 280) and the determination of the region of interest 190 (step 282) may be performed by using corrected images. Further, as outlined above with respect to the curves depicted in FIG. 17, the measurement of reaction kinetics 284 may be performed by using corrected images, as well as the analysis of measurement results (step 286) and the measurement statistics (step 288). Thus, the above-mentioned correction algorithm may be beneficial in one, more than one or even all method steps of the exemplary embodiment of the method for determining the concentration of at least one analyte in a sample of a body fluid as depicted in FIG. 18.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

LIST OF REFERENCE NUMBERS 110 test system
112 device
114 magazine
116 receptacle
118 control unit
120 processor
122 user interface
124 test element
126 application position
128 magazine housing
130 housing
132 lower shell
134 upper shell
136 sealing film
138 adhesive
140 puncture element
142 micro-sampler
144 lancet
146 lancet tip
148 capillary channel
150 test chemistry ring
152 test chemistry carrier
154 test chemistry
156 adhesive
158 cavity
160 window
162 test field
164 engagement opening
166 actuator
168 puncture opening
170 viewing window
172 application side
174 detection side
176 detector
178 image detector
180 photosensitive element
182 light source
184 optical element
186 image
188 wetted portion
190 region of interest (ROI)
192 acquisition of new image
194 correction step
196 detect characteristic feature
198 correction
200 portion
202 characteristic feature
204 search region
206 create corrected image
208 repetition
210 further evaluation
212 boundaries
214 detection of sample application
216 peak
218 moment of sample application
220 no sample application detected
222 add new image to preliminary averaged blank image
224 sample application detected
226 define averaged blank image
228 background region
230 unwetted test field
232 region of significant changes
234 image of changes
236 average values of lines
238 average values of columns
242 threshold
244 threshold
246 image of changes
248 histogram
250 threshold
252 class of information values below threshold
254 class of information values above threshold
256 binary mask
258 bubbles or debris
260 20 mg/dl
262 70 mg/dl
264 150 mg/dl
266 250 mg/dl
268 550 mg/dl
270 start
272 detect test field
274 detect moment of sample application
276 detect blank image
278 detect significant changes
280 process significant changes
282 determine ROI
284 measure reaction kinetics
286 analysis of measurement
288 measurement statistics
290 end

The invention claimed is:

1. A method for detecting at least one analyte in at least one sample of a body fluid, wherein at least one test element with at least one test field is used, the at least one test field having at least one test chemistry, wherein the test chemistry is adapted to perform at least one optically detectable detection reaction in the presence of the analyte, wherein the method comprises acquiring an image sequence of images of the test field by using at least one image detector, wherein each image comprises a plurality of pixels, wherein the method further comprises detecting using a control unit at least one characteristic feature of the test field in the images of the image sequence, wherein the method further comprises correcting using the control unit a relative position change between the image detector and the test field in the image sequence by using the characteristic feature, thereby obtaining a sequence of corrected images, wherein the sequence of corrected images is adapted for observing a time-dependent change of at least one optically detectable property of the test field due to the detection reaction of the test chemistry with the analyte to be detected.

2. The method according to claim 1, wherein the detecting of the characteristic feature comprises selecting at least one specific part of one or more images of the image sequence, denoting the information contained in this part as the characteristic feature, wherein other images of the image sequence are scanned or searched for this information or similar types of information.

3. The method according to claim 1, wherein the correction is individually adapted for each image of the image sequence, according to the characteristic feature detected in the specific image.

4. The method according to claim 1, wherein the correction of the relative position change comprises using at least one image of the image sequence as a reference image, wherein the reference image is kept unchanged, wherein the remaining images of the image sequence are corrected by using at least one calculational correction of the position of the pixels, wherein the calculational correction is chosen such that a correlation between the reference image and the corrected remaining images of the image sequence is maximized.

5. The method according to claim 4, wherein the calculational correction comprises at least one of the following:
- a shifting of the pixels of the remaining images of the image sequence in at least one spatial direction, wherein the shifting is chosen such that the correlation between the reference image and the corrected remaining images is maximized; or
- at least one rotation of the remaining images of the image sequence about at least one rotational axis by at least one rotation angle, wherein one or both of the rotational axis and the rotation angle are chosen such that the correlation between the reference image and the corrected remaining images is maximized.

6. The method according to claim 1, wherein the characteristic feature comprises at least one feature selected from the group consisting of: a roughness of the test field detectable in the images of the image sequence; a granularity of the test chemistry of the test field detectable in the images of the image sequence; faults of the test field detectable in the images of the image sequence; at least one fiducial mark comprised in the test field and detectable in the images of the image sequence.

7. The method according to claim 6, wherein the characteristic feature comprises at least two fiducial marks comprised in the test field and detectable in the images of the image sequence.

8. The method according to claim 1, wherein the sample of the body fluid is applied to the test field during acquisition of the image sequence, wherein at least one touchdown image is detected in the image sequence, wherein the touchdown image is an image of the image sequence acquired at a point in time closest to the moment of application of the sample of the body fluid onto the test field.

9. The method according to claim 1, wherein the sample of the body fluid is applied to the test field during acquisition of the image sequence, wherein the image sequence comprises a blank image sequence, wherein the blank image sequence comprises a plurality of blank images acquired before applying the sample of the body fluid to the test field, wherein at least one averaged blank image is derived from the blank images of the blank image sequence after performing the correction of the relative position change of the blank images of the blank image sequence.

10. The method according to claim 9, wherein the averaged blank image is derived in a continuous process during acquiring the images of the image sequence, wherein a preliminary averaged blank image is derived from the corrected blank images acquired so far, wherein new acquired blank images are used for revising the preliminary averaged blank image.

11. The method according to claim 9, wherein the analyte is detected by comparing the images of the sequence of corrected images with one or both of a touchdown image and the blank image sequence, wherein the comparison is performed on a pixel-by-pixel basis.

12. The method according to claim 11, wherein at least one averaged normalized value is created over at least part of the sequence of corrected relative images, wherein the averaged normalized value is monitored as a function of time after application of the sample of the body fluid to the test field.

13. The method according to claim 1, wherein one or both of boundaries of the test field and boundaries of a visible window of the test field are detected in the sequence of corrected images.

14. The method according to claim 1, wherein a moment of application of the sample of the body fluid onto the test field is detected in the image sequence.

15. The method according to claim 1, wherein after application of the sample of the body fluid onto the test field at least one region of interest is determined in the image sequence.

16. The method according to claim 15, wherein at least one corrected image acquired before or during application of the sample of the body fluid onto the test field is compared to at least one corrected image acquired after application of the sample of the body fluid onto the test field on a pixel-by-pixel basis, thereby generating a difference value for each pixel, wherein the difference value denotes a difference of the information contained in corresponding pixels of the corrected images acquired before or during and after application of the sample of the body fluid onto the test field, wherein the pixels are classified as pixels belonging to the region of interest or as pixels not belonging to the region of interest based on the difference values.

17. The method according to claim 15, wherein an image mask is generated denoting the pixels belonging to the region of interest.

18. A device for detecting at least one analyte in at least one sample of a body fluid, wherein the device comprises at least one test element receptacle for receiving at least one test element having at least one test field with at least one test chemistry, wherein the device further comprises at least one image detector for acquiring an image sequence of images of the test field, wherein the device further comprises at least one control unit, wherein the control unit is adapted to:
- acquire an image sequence of images of the test field by using at least one image detector, wherein each image comprises a plurality of pixels,
- detecting at least one characteristic feature of the test field in the images of the image sequence, and
- correct a relative position change between the image detector and the test field in the image sequence by using the characteristic feature, thereby obtaining a sequence of corrected images, wherein the sequence of corrected images is adapted for observing a time-dependent change of at least one optically detectable property of the test field due to the detection reaction of the test chemistry with the analyte to be detected.

19. A test system for detecting at least one analyte in at least one sample of a body fluid, the test system comprising: at least one device for detecting at least one analyte in at least one sample of a body fluid and at least one test element having at least one test field with at least one test chemistry, wherein the test chemistry is adapted to perform at least one optically detectable detection reaction in the presence of the analyte, wherein the device comprises at least one test element receptacle for receiving at least one test element having at least one test field with at least one test chemistry, wherein the device further comprises at least one image detector for acquiring an image sequence of images of the test field, wherein the device further comprises at least one control unit, wherein the control unit is adapted to:

acquire an image sequence of images of the test field by using at least one image detector, wherein each image comprises a plurality of pixels, detecting at least one characteristic feature of the test field in the images of the image sequence, and correct a relative position change between the image detector and the test field in the image sequence by using the characteristic feature, thereby obtaining a sequence of corrected images, wherein the sequence of corrected images is adapted for observing a time-dependent change of at least one optically detectable property of the test field due to the detection reaction of the test chemistry with the analyte to be detected.

20. The test system according to claim 19, wherein the test system further comprises at least one puncture element, wherein the test system is adapted to puncture at least one skin portion of a user by using the puncture element, thereby creating the sample of the body fluid, wherein the test system is further adapted to transfer the sample of the body fluid onto the test field of the test element.

* * * * *